United States Patent
Lindsey et al.

(10) Patent No.: US 11,077,604 B2
(45) Date of Patent: Aug. 3, 2021

(54) POLYMERIC TUBES WITH CONTROLLED ORIENTATION

(71) Applicant: Zeus Industrial Products, Inc., Orangeburg, SC (US)

(72) Inventors: James M. Lindsey, Lexington, SC (US); John Richard Campanelli, Greer, SC (US); Elizabeth A. Foley, Columbia, SC (US); Bruce L. Anneaux, Lexington, SC (US); Justin A. Marro, Orangeburg, SC (US)

(73) Assignee: Zeus Industrial Products, Inc., Orangeburg, SC (US)

( * ) Notice: Subject to any disclaimer, the term of this patent is extended or adjusted under 35 U.S.C. 154(b) by 65 days.

(21) Appl. No.: 16/148,826

(22) Filed: Oct. 1, 2018

(65) Prior Publication Data

US 2019/0077067 A1 Mar. 14, 2019

Related U.S. Application Data

(63) Continuation-in-part of application No. 16/124,398, filed on Sep. 7, 2018, now abandoned.
(Continued)

(51) Int. Cl.
*B29C 55/26* (2006.01)
*A61L 31/14* (2006.01)
(Continued)

(52) U.S. Cl.
CPC .............. *B29C 55/26* (2013.01); *A61L 31/06* (2013.01); *A61L 31/129* (2013.01); *A61L 31/14* (2013.01);
(Continued)

(58) Field of Classification Search
CPC .......... B29C 55/26; A61L 31/06; A61L 31/14; A61L 31/16; B29K 2067/046
See application file for complete search history.

(56) References Cited

U.S. PATENT DOCUMENTS

| 4,478,898 A | 10/1984 | Kato |
| 5,637,113 A | 6/1997 | Tartaglia et al. |

(Continued)

FOREIGN PATENT DOCUMENTS

| JP | 10-138336 A | 5/1998 |
| JP | 11-268116 | 10/2011 |
| KR | 10-1999-0001611 A | 1/1999 |

OTHER PUBLICATIONS

PCT International Search Report & Written Opinion dated Apr. 12, 2019, which issued for corresponding PCT Application No. PCT/IB2018/057622.
(Continued)

*Primary Examiner* — Jeffry H Aftergut
(74) *Attorney, Agent, or Firm* — Womble Bond Dickinson (US) LLP

(57) ABSTRACT

Methods for preparing oriented polymer tubes, such as biodegradable polymer tubes suitable for in vivo use, are provided herein. The disclosed methods provide alternatives to the typical extrusion/expansion methods by which oriented polymeric tubes for such uses are commonly produced. Advantageously, the disclosed methods can provide more homogeneous molecular orientation of crystallizable
(Continued)

polymers within the tube walls, which can endow such polymeric tubes with enhanced strength (e.g., resistance to compression) and toughness.

30 Claims, 15 Drawing Sheets

Related U.S. Application Data

(60) Provisional application No. 62/555,796, filed on Sep. 8, 2017.

(51) Int. Cl.
    *A61L 31/12*     (2006.01)
    *A61L 31/06*     (2006.01)
    *A61L 31/16*     (2006.01)
    *B29K 67/00*     (2006.01)
    *B29L 31/00*     (2006.01)

(52) U.S. Cl.
    CPC .............. *A61L 31/148* (2013.01); *A61L 31/16* (2013.01); *B29K 2067/046* (2013.01); *B29K 2995/006* (2013.01); *B29K 2995/0053* (2013.01); *B29L 2031/7534* (2013.01)

(56) References Cited

U.S. PATENT DOCUMENTS

| | | | |
|---|---|---|---|
| 6,290,722 | B1 | 9/2001 | Wang |
| 6,626,939 | B1* | 9/2003 | Burnside ............... A61L 31/148 |
| | | | 623/1.38 |
| 8,241,554 | B1* | 8/2012 | Abbate ................... A61F 2/915 |
| | | | 264/573 |
| 2004/0044397 | A1* | 3/2004 | Stinson ..................... A61F 2/06 |
| | | | 623/1.15 |
| 2005/0137678 | A1 | 6/2005 | Varma |
| 2006/0255497 | A1 | 11/2006 | Prevotat |
| 2007/0207186 | A1* | 9/2007 | Scanlon ................... A61F 2/91 |
| | | | 424/424 |
| 2011/0189475 | A1 | 8/2011 | Rizk et al. |
| 2016/0263357 | A1 | 9/2016 | Lee et al. |

OTHER PUBLICATIONS

PCT International Search Report & Written Opinion dated Jan. 11, 2019, which issued for corresponding PCT Application No. PCT/US2018/049850.

\* cited by examiner

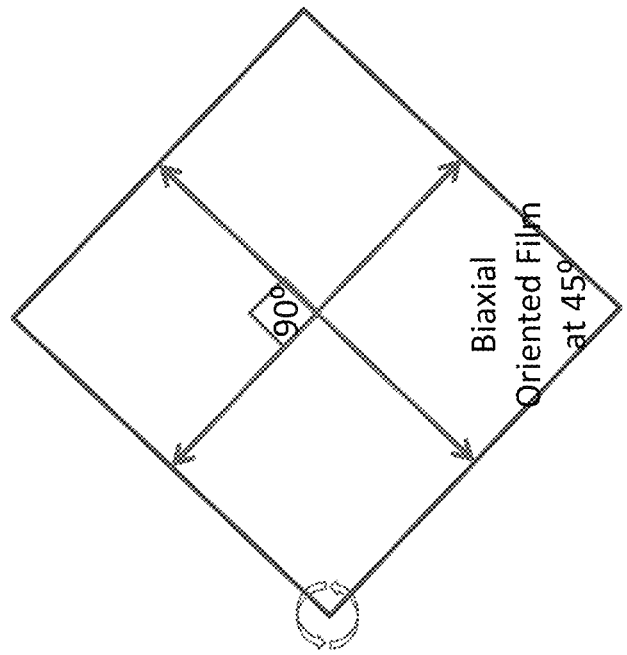
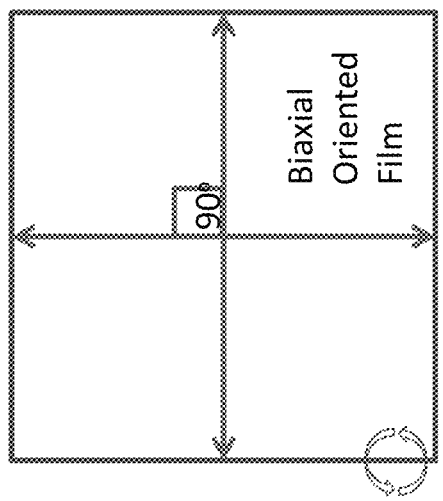
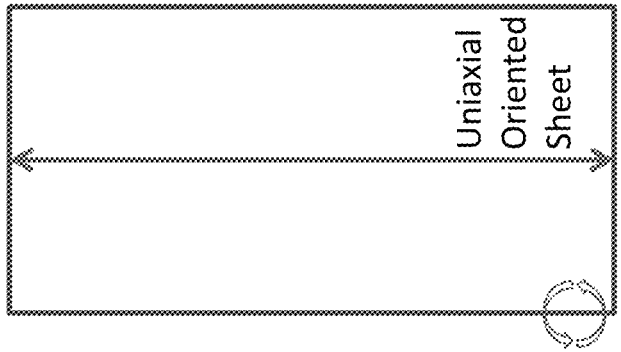
FIGURE 3C
FIGURE 3B
FIGURE 3A

POLYMERIC TUBES WITH CONTROLLED ORIENTATION

CROSS-REFERENCE TO RELATED APPLICATIONS

The present application claims priority to U.S. Provisional Patent Application 62/555,796, filed Sep. 8, 2017, which is incorporated herein by reference in its entirety.

FIELD OF THE INVENTION

The present application is directed to polymeric tubes with particular molecular orientations, which find application in a variety of fields.

BACKGROUND OF THE INVENTION

Polymeric tubes are widely used for a number of applications. Polymeric bioabsorbable tubes, in particular, can be designed for implantation within the body (e.g., within blood vessels and arteries) to serve as scaffolds to replace traditional metal stents. Some polymeric bioabsorbable tubes find use as nerve guide tubes and/or as placeholders within the body for regeneration of nerve tissue. Other polymeric bioabsorbable tubes can be designed as drainage tubes for the evacuation of fluids and/or gases from a body cavity or wound, e.g., to promote healing. Advantageously, polymeric bioabsorbable tubes are prepared with biodegradable polymer(s) and thus, can dissolve or be absorbed by the body over time, eliminating the need for surgical removal of the tubes after use.

Polymeric biodegradable tubes generally comprise one or more biodegradable polymers, e.g., including, but not limited to, poly(L-lactide) (PLLA), poly(D-lactide) (PDLA), poly(D,L-lactide) (PDLLA), poly(E-caprolactone) (PCL), polyglycolic acid (PGA), poly(para-dioxanone) (PDO), poly(trimethylene carbonate) (PTMC), poly(hydroxybutyrate), poly(hydroxyvalerate), poly(tetramethyl carbonate), poly(ethylene oxide) (PEO), poly(ethylene glycol) (PEG), poly(propylene glycol) (PPG), and copolymers, blends, and derivatives thereof. Selection of the polymer or polymers to produce a polymeric bioabsorbable tube can have implications on both the biocompatibility/toxicity properties of the resulting tube and the physical/mechanical properties of the resulting tube, e.g., rate of degradation, strength (e.g., radial strength), and recoil rate.

One common means for producing such polymeric tubes (and, in particular, single-layer, thick-walled polymeric tubes) involves extrusion and annular expansion processes. Using such methods, a polymer is extruded into a tubular form, and the resulting tubular form is stretched/expanded annularly to provide a polymeric tube. Molecular orientation within the polymeric tube wall, as provided by the annular expansion, is generally advantageous as it leads to increased strength and/or heat shrinkable properties. However, known extrusion and annular expansion processes are inherently limited as to the degree of molecular orientation possible throughout the wall thickness of the polymeric tube. Further, due to the tubular structure, a gradient of molecular orientation may be present throughout the thickness of the wall, as with annular expansion, the inside diameter of a tube is generally subjected to greater stretching/molecular orientation than the outside diameter of the tube. As such, it would be beneficial to provide methods for controlling the molecular orientation within polymeric tube walls and to provide polymeric tubes with walls exhibiting such controlled molecular orientation.

SUMMARY OF THE INVENTION

The present invention relates generally to methods for the production of polymeric tubes and to polymeric tubes produced by such methods. Polymeric tubes for use, e.g., in biomedical applications, are generally expanded/stretched in some fashion to induce molecular orientation within the tube walls, which affords increased strength (e.g., resistance to radial compression). The novel methods disclosed herein, involving producing polymeric tubes and molecularly orienting the polymers therein to give oriented polymeric tubes, advantageously employ planar stretching and/or multi-layer annular expansion processes. As will be disclosed herein, by modifying the process by which molecules are oriented within a polymeric tube (with respect to the typical extrusion/annular expansion method for providing such oriented polymeric tubes), tubes can be provided which exhibit modified crystallinity characteristics and, in some embodiments, corresponding enhanced strength (e.g., enhanced resistance to radial compression) and/or controlled heat shrinkable properties.

In one aspect, the present disclosure provides a method for producing an oriented polymeric tube, comprising: subjecting a polymeric material comprising a crystallizable biodegradable polymer and having a first dimension to planar stretching to increase the first dimension to give a stretched polymeric material exhibiting at least partial molecular orientation; and forming the stretched polymeric material and an adhesive polymeric material into a tubular form, (which can also be referred to as a tube or an oriented polymeric tube). As an example, the adhesive polymeric material adheres adjacent layers of the stretched polymeric material to itself or to other layers within the tubular form. The polymeric material can, in some embodiments, be a polymer film and, in some embodiments, can be a polymer profile.

In certain embodiments, the polymeric material has a second dimension and the subjecting step further comprises stretching the polymeric material to increase the second dimension to give a biaxially oriented polymeric material. The adhesive polymer material can be associated with the crystallizable biodegradable polymer at varying stages of the disclosed method. For example, in one embodiment, the above method further comprises combining the adhesive polymeric material with the crystallizable biodegradable polymer prior to the subjecting step to give a polymeric material that is a composite polymeric material with the crystallizable biodegradable polymer and adhesive polymeric material in layered form. In another embodiment, the above method further comprises combining the adhesive polymeric material with the stretched polymeric material prior to the forming step.

The forming step, in certain embodiments, comprises wrapping the polymeric material and adhesive polymeric material around a cylindrical form. In some embodiments, such wrapping comprises wrapping the polymeric material and adhesive polymeric material around the cylindrical form multiple times, giving a tube comprising multiple layers of the stretched polymeric material and multiple layers of the adhesive polymeric material. The cylindrical form can vary and can be, e.g., a mandrel, wherein the method further comprises removing the tube from the mandrel. In some embodiments, the cylindrical form comprises a device.

In another aspect, the disclosure provides a method for producing an oriented polymeric tube, comprising: obtaining at least two polymeric tubes, each polymeric tube comprising a crystallizable biodegradable polymer; annularly expanding the at least two polymeric tubes to produce at least two oriented polymeric tubes; and combining the at least two oriented polymeric tubes and one or more adhesive polymeric materials into a multi-layer tubular form. In some embodiments, the annular expansion step is done before the combining step. In some embodiments, the combining step is done before the annular expansion step, and in some embodiments, the combining step is done during the annular expansion step (i.e., the at least two oriented polymeric tubes and the adhesive polymeric materials are combined during the annular expansion of the at least two polymeric tubes).

This method can, in some embodiments, further comprise combining the adhesive polymeric material with one or more of the at least two polymeric tubes prior to the annular expansion step to give one or more polymeric tubes that are composite polymeric tubes, with the crystallizable biodegradable polymer and the adhesive polymeric material in layered form. The method can, in some embodiments, further comprise combining the adhesive polymeric material with one or more of the at least two polymeric tubes (prior to or after the annular expansion step) to give one or more polymeric tubes that are composite polymeric tubes with the crystallizable biodegradable polymer and the adhesive polymeric material in layered form. In certain embodiments, the method referenced above and described in more detail herein below further comprise a step of fusing the tubular form by subjecting the multi-layer tubular form to heat, pressure, or both heat and pressure. Pressure can be either positive or negative pressure, e.g., including pulling a vacuum to form the tube (such as by applying vacuum through a perforated mandrel). The fusing step may, for example, comprise applying a shrink tube or shrink film around the tubular form to give a layered structure before subjecting the tubular form/layered structure to heat, pressure, or both heat and pressure. The composition of the shrink tube or shrink film can vary and can comprise one or more materials selected, for example, from the group consisting of fluoropolymers (e.g., poly(tetrafluoroethylene)), polyolefins (e.g., low-density polyethylene (LLDPE)), polyurethanes, and/or silicone polymers (e.g., polydimethylsiloxane, PDMS) and combinations thereof.

In the context of any of the methods disclosed herein, the crystallizable biodegradable polymer in certain embodiments is selected from the group consisting of poly(L-lactide) (PLLA), poly(D-lactide) (PDLA), poly(ε-caprolactone) (PCL), polyglycolic acid (PGA), poly(para-dioxanone) (PDO), poly(hydroxybutyrate), poly(hydroxyvalerate), poly(tetramethyl carbonate), poly(ethylene oxide) (PEO), poly(ethylene glycol) (PEG), poly(propylene glycol) (PPG), and copolymers, blends, and derivatives thereof. The adhesive polymeric material is selected, for example, from the group consisting of poly(ε-caprolactone), poly(trimethylene carbonate), poly(D,L-Lactide) (PDLLA), poly(L-Lactide-co-ε-caprolactone), poly(L-Lactide-co-trimethylene carbonate), poly(ε-caprolactone-co-trimethylene carbonate), poly(ethylene glycol), poly(L-lactide-co-poly(ethylene glycol)), and copolymers and derivatives and combinations thereof. It is noted that these lists are not intended to be exclusive, i.e., the same polymer or polymers may be present as both a crystallizable biodegradable polymer and as an adhesive polymer within a given product, which may vary with respect to molecular orientation (e.g., where the polymer has greater molecular orientation as the crystallizable biodegradable polymer component and lesser molecular orientation as the adhesive polymer component). As such, the disclosure encompasses, in certain embodiments, methods and products wherein the crystallizable biodegradable polymer and the adhesive polymeric material comprise the same polymer with different orientations (e.g., different amounts of orientation).

The present disclosure further provides oriented polymeric tubes prepared according to any of the methods disclosed herein. Some such oriented polymeric tubes primarily comprise the crystallizable biodegradable polymer, with a minimal amount of adhesive polymeric material. In some embodiments, such oriented polymeric tubes are characterized by molecular orientation of the crystallizable biodegradable polymer that is substantially consistent through a wall of the oriented polymer tube.

A further aspect provides a method for producing an oriented polymeric tube, comprising: determining a desired geometry and molecular orientation profile for the oriented polymeric tube; selecting one or more polymeric tube precursors comprising a biodegradable, crystallizable polymer; positioning the one or more polymeric tube precursors; and forming the one or more polymeric tube precursors into the oriented polymeric tube exhibiting the desired final tubular geometry and molecular orientation profile. The geometry and molecular orientation profile can be determined, e.g., based on one or more of: (i) a desired mechanical property of the oriented polymer tube to be formed; (ii) a desired thermodynamic property of the oriented polymer tube to be formed; and (iii) a desired chemical property of the oriented polymer tube to be formed.

In some embodiments, at least one of the one or more polymeric precursors are selected based at least in part on: (i) a composition of the one or more polymeric precursors, (ii) a geometry of the one or more polymeric precursors, (iii) a mechanical property of the one or more polymeric precursors, (iv) a thermodynamic property of the one or more polymeric precursors, (v) a chemical property of the one or more polymeric precursors, (vi) a degree of molecular orientation of the one or more polymeric precursors, (vii) a molecular orientation profile with respect to one or more axes of the one or more polymeric precursors, (viii) a predetermined method of forming the final polymeric tube from the one or more polymeric precursors, and any combination thereof. In some embodiments, the one or more polymeric precursors are selected from the group consisting of: (i) one or more films, (ii) one or more tubes, and (iii) one or more profiles.

In particular embodiments, the one or more polymeric precursors are one or more films or one or more tubes, and wherein the films or tubes are specifically selected to contribute to the oriented polymeric tube one or more of: (i) one or more specific mechanical properties, (ii) one or more specific thermodynamic properties, (iii) one or more specific chemical properties, and (iv) one or more specific degradation rates. In other particular embodiments, the one or more polymeric precursors are one or more profiles, and wherein the one or more profiles have cross-sectional shapes including but not limited to round, rectangular, triangular, elliptical, and tubular. In some embodiments, the one or more polymeric precursors are one or more profiles, and wherein the profiles are specifically selected to contribute to the oriented polymeric tube one or more of: (i) one or more specific mechanical properties, (ii) one or more specific thermodynamic properties, (iii) one or more specific chemical properties, and (iv) one or more specific degradation rates. Advantageously, in some of these embodiments, the one or more polymeric precursors further comprise a tie layer.

The positioning of the one or more polymeric precursors, in some embodiments, comprises one or more of: (i) positioning the one or more polymeric precursors around a mandrel (or other support, as described herein below), and (ii) positioning the one or more polymeric precursors inside a mold (which may be, in certain embodiments, expandable, e.g., comprising a balloon). Positioning around a mandrel can comprise, for example, positioning around a mandrel using a technique selected from the group consisting of wrapping, sheathing, winding, braiding, and combinations thereof. The mandrel can, in some embodiments, comprise a device. Positioning of the one or more polymeric precursors inside the mold comprises: (i) positioning the one or more polymeric precursors on a mandrel and then inserting the one or more polymeric precursors on the mandrel into the mold, and removing the mandrel, (ii) positioning the one or more polymeric precursors on a mandrel, and then removing the mandrel and inserting the one or more polymeric precursors into the mold, or (iii) positioning the one or more polymeric precursors inside the mold during one or more production steps of the precursor.

The one or more production steps are selected, for example, from the group consisting of tube expansion, blow molding, injection-stretch blow molding, die drawing, and mandrel drawing. The positioning comprises, for example, positioning of two or more polymeric precursors, wherein the positioning of each polymeric precursor occurs simultaneously or sequentially. The forming can, in certain embodiments, further comprise fusing the one or more polymeric precursors by subjecting the one or more polymeric precursors to heat, pressure, or both heat and pressure. Such fusing can comprise, for example, applying a shrink tube or shrink film around the one or more polymeric precursors prior to subjecting the one or more polymeric precursors to heat, pressure, or both heat and pressure. Such fusing can comprise, for example, subjecting the one or more polymeric precursors to heat, pressure, or both heat and pressure using a mold and a balloon. In some such embodiments, the mold is lined with the one or more polymeric precursors and a portion of the balloon will make up a portion of the final polymeric tube. In such embodiments, the forming step can occur, e.g., during or after the positioning step. In some embodiments, two or more positioning steps and two or more forming steps occur simultaneously or sequentially. Advantageously, in some embodiments, the one or more polymeric precursors comprise a biocompatible, biodegradable polymer, such as polymers including, but not limited to, one or more polymers selected from the group consisting of poly(L-lactide) (PLLA), poly (D-lactide) (PDLA), poly(ε-caprolactone) (PCL), polyglycolic acid (PGA), poly(para-dioxanone) (PDO), poly(hydroxybutyrate), poly(hydroxyvalerate), poly(tetramethyl carbonate), poly(ethylene oxide) (PEO), poly(ethylene glycol) (PEG), poly(propylene glycol) (PPG) and copolymers, blends, and derivatives thereof.

The disclosure further provides an oriented polymeric tube prepared according to any of the methods outlined herein. Tubes according to the present disclosure can be characterized, e.g., by a molecular orientation profile that is substantially consistent through a wall of the oriented polymeric tube, a molecular orientation profile that is substantially consistent through predefined portions of a wall of the oriented polymeric tube, a molecular orientation profile characterized by varying levels of orientation through predefined portions of a wall of the oriented polymeric tube, a molecular orientation profile characterized by varying axes of orientation through predefined portions of a wall of the oriented polymeric tube, a molecular orientation profile characterized by an increasing molecular orientation gradient through a wall from the inner diameter to the outer diameter of the oriented polymeric tube, a molecular orientation profile characterized by a decreasing molecular orientation gradient through a wall from the inner diameter to the outer diameter of the oriented polymeric tube, a molecular orientation profile that is substantially consistent through a length of the oriented polymeric tube, a molecular orientation profile that is substantially consistent through predefined portions of a length of the oriented polymeric tube, a molecular orientation profile characterized by varying levels of orientation through predefined portions of a length of the oriented polymeric tube, and/or a molecular orientation profile characterized by varying axes of orientation through predefined portions of a length of the oriented polymeric tube.

Tubes according to the present disclosure can be characterized, e.g., by a compositional profile that is substantially consistent through a wall of the oriented polymeric tube, by a compositional profile that is substantially consistent through predefined portions of a wall of the oriented polymeric tube, a compositional profile characterized by varying compositions through predefined portions of a wall of the oriented polymeric tube, a compositional profile that is substantially consistent through a length of the oriented polymeric tube, a compositional profile that is substantially consistent through predefined portions of a length of the oriented polymeric tube, and/or a compositional profile characterized by varying compositions through predefined portions of a length of the oriented polymeric tube. Tubes according to the present disclosure can be characterized, e.g., by a degradation rate profile that is substantially consistent through a wall of the oriented polymeric tube, a degradation rate profile that is substantially consistent through predefined portions of a wall of the polymeric tube, a degradation rate profile characterized by varying degradation rates through predefined portions of a wall of the oriented polymeric tube, a degradation rate profile characterized by an increasing degradation rate gradient through a wall from the inner diameter to the outer diameter of the polymeric tube, a degradation rate profile characterized by a decreasing degradation rate gradient through a wall from the inner diameter to the outer diameter of the oriented polymeric tube, a degradation rate profile that is substantially consistent through a length of the oriented polymeric tube, a degradation rate profile that is substantially consistent through predefined portions of a length of the oriented polymeric tube, a degradation rate profile characterized by varying degradation rates through predefined portions of a length of the oriented polymeric tube, and/or a degradation rate profile characterized by a degradation rate gradient along the length of the oriented polymeric tube.

The disclosure further provides a method for producing an oriented polymeric tube, comprising: determining a desired tubular geometry and at least one of a desired compositional profile and a desired molecular orientation profile; selecting one or more polymeric precursors; positioning the one or more polymeric precursors; and forming the one or more polymeric precursors into the oriented polymeric tube exhibiting the desired tubular geometry and at least one of the desired compositional profile and the desired molecular orientation profile. Certain specific embodiments are as follows:

Embodiment 1: A method for producing an oriented polymeric tube, comprising: obtaining at least one stretched polymeric material exhibiting at least partial molecular orientation, wherein: the obtaining the at least one stretched polymeric material comprising stretching at least one polymeric material, the at least one polymeric material comprising a first dimension, and at least one crystallizable biodegradable polymeric material, and the at least one polymeric material being stretched in a manner that increases the first dimension; and forming the oriented polymeric tube using the at least one stretched polymeric material.

Embodiment 2: The method of the preceding embodiment, wherein the stretching comprises planar stretching.

Embodiment 3: The method of any preceding embodiment, wherein one or more of the at least one polymeric material is one or more of a polymer film, a polymer monofilament, a polymer ribbon, a polymer tape, and a polymer rod.

Embodiment 4: The method of any preceding embodiment, wherein: the at least one polymeric material has a second dimension, and the stretching the at least one polymeric material comprises stretching the at least one polymeric material to increase the second dimension, wherein the at least one stretched polymeric material comprises a biaxially stretched polymeric material.

Embodiment 5: The method of any preceding embodiment, wherein the forming comprises using the at least one stretched polymeric material and at least one adhesive polymeric material.

Embodiment 6: The method of the preceding embodiment, further comprising: obtaining the at least one polymeric material based at least in part on combining the at least one adhesive polymeric material with the at least one crystallizable biodegradable polymeric material.

Embodiment 7: The method of the preceding embodiment, wherein the at least one polymeric material is a composite polymeric material comprising the at least one crystallizable biodegradable polymeric material and the at least one adhesive polymeric material in layered form.

Embodiment 8: The method of Embodiment 6, wherein the at least one adhesive polymeric material and the at least one crystallizable biodegradable polymeric material are combined before, during, or after the at least one polymeric material is stretched.

Embodiment 9: The method of Embodiment 6, wherein the forming the tube comprises wrapping the at least one stretched polymeric material and the at least one adhesive polymeric material around a support.

Embodiment 10: The method of the preceding embodiment, wherein the support has one or more of a cylindrical shape, a round shape, a rectangular shape, a triangular shape, an elliptical shape, a polygonal shape, and a tubular form.

Embodiment 11: The method of Embodiment 9 or 10, wherein the wrapping comprises wrapping the at least one stretched polymeric material and the at least one adhesive polymeric material around the support multiple times such that the tube comprises multiple layers of the at least one stretched polymeric material and multiple layers of the at least one adhesive polymeric material.

Embodiment 12: The method of any of Embodiments 9-11, wherein: the at least one stretched polymeric material comprises a plurality of units of stretched polymeric material, the plurality of units of stretched polymeric material comprises different polymeric materials or a same polymeric material; and the forming comprises arranging the plurality of units of stretched polymeric material in at least one of a stacked manner and a staggered manner, and wrapping the arranged plurality of units of stretched polymeric material on a bias angle.

Embodiment 13: The method of any of Embodiments 9-12, wherein the support is a mandrel, and the method further comprises removing the tube from the mandrel.

Embodiment 14: The method of any of Embodiments 9-12, wherein the support comprises a device.

Embodiment 15: The method of Embodiment 14, further comprising forming a resulting composite based at least in part on the oriented polymeric tube and the support, and the resulting composite is a medical device.

Embodiment 16: The method of any preceding embodiment, further comprising forming a medical device based at least in part on the oriented polymeric tube.

Embodiment 17: The method of the preceding embodiment, wherein the forming the medical device comprises: cutting the tube into a stent.

Embodiment 18: The method of the preceding embodiment, further comprising applying one or more of a therapeutic, a covering, and a coating to the stent.

Embodiment 19: The method of any preceding embodiment, wherein the forming comprises subjecting the at least one stretched polymeric material to at least one of heat and pressure.

Embodiment 20: The method of any preceding embodiment, wherein the forming comprises: forming a layered structure, the forming the layered structure comprising: applying a shrink tube or shrink film around at least part of the at least one stretched polymeric material to give a layered structure, and subjecting the layered structure to at least one of heat and pressure.

Embodiment 21: The method of any preceding embodiment, wherein the forming comprises: inserting at least part of the at least one stretched polymeric material in a mold; positioning the at least one stretched polymeric material over an expandable support; and subjecting the at least one stretched polymeric material to at least one of heat and pressure.

Embodiment 22: The method of any preceding embodiment, wherein one or more of the at least one crystallizable biodegradable polymeric material is selected from the group consisting of poly(L-lactide) (PLLA), poly(D-lactide) (PDLA), poly(ε-caprolactone) (PCL), polyglycolic acid (PGA), poly(para-dioxanone) (PDO), poly(hydroxybutyrate), poly(hydroxyvalerate), poly(tetramethyl carbonate), poly(ethylene oxide) (PEO), poly(ethylene glycol) (PEG), poly(propylene glycol) (PPG), and copolymers and derivatives and combinations thereof.

Embodiment 23: The method of any preceding embodiment, wherein the forming comprises using the at least one stretched polymeric material and at least one adhesive polymeric material, and wherein the adhesive polymeric material is selected from the group consisting of poly(ε-caprolactone), poly(trimethylene carbonate), poly(D,L-lactide), poly(L-lactide)-co-ε-caprolactone), poly(L-lactide-co-trimethylene carbonate), poly(ε-caprolactone-co-trimethylene carbonate), poly(ethylene glycol), poly(L-lactide-co-poly(ethylene glycol)), and copolymers and derivatives and combinations thereof.

Embodiment 24: The method of any of Embodiments 5-23, wherein the forming comprises using the at least one stretched polymeric material and at least one adhesive polymeric material, and the at least one crystallizable biodegradable polymeric material and the at least one adhesive polymeric material comprise a same polymeric material.

Embodiment 25: The method of any preceding embodiment, wherein the at least one stretched polymeric material is stretched at least ten percent of a maximum stretch ratio respectively corresponding to the at least one polymeric material.

Embodiment 26: The method of any preceding embodiment, wherein the stretching the at least one polymeric material comprises controlling, during the stretching, one or more of a mechanical property, a thermodynamic property, a chemical property, an electrical property, and a degradation rate, of the at least one polymeric material.

Embodiment 27: The method of any preceding embodiment, wherein the at least one polymeric material is stretched between three hundred percent and one thousand percent of an original dimension of the at least one polymeric material.

Embodiment 28: A method, comprising: obtaining at least one stretched polymeric material exhibiting at least partial molecular orientation, wherein: the at least one stretched polymeric material corresponds to at least one polymeric material comprising a first dimension, and at least one crystallizable biodegradable polymeric material, and the at least one polymeric material having been stretched in a manner that increased the first dimension; and forming a tube using the at least one stretched polymeric material.

Embodiment 29: A tube, comprising: at least one stretched polymeric material exhibiting at least partial molecular orientation, the at least one stretched polymeric material being obtained based at least in part on stretching at least one polymeric material, wherein the at least one polymeric material comprises a first dimension, and at least one crystallizable biodegradable polymeric material, the at least one polymeric material, and wherein the at least one polymeric material is stretched in a manner that increases the first direction.

Embodiment 30: A tube, wherein: the tube comprises at least one crystallizable biodegradable polymeric material, and an outer surface that has a normal that is perpendicular to a length of the tube, and the tube exhibits: a maximum stress value of about 20 MPa or greater measured based on a first compression cycle; and the tube being deformed 17% or less in at least a first dimension after the first compression cycle.

Embodiment 31: The tube of the preceding embodiment, wherein the first compression cycle comprises: obtaining an initial distance between two parallel plates between which the tube is disposed, the two parallel plates contacting the outer surface of the tube in a manner in which the two parallel plates provide substantially no load on the tube; compressing the plates to a distance that is 50% of the initial distance at a rate of 50% of the initial distance of the two parallel plates per minute, the compressing the plates causing the tube to deform in the first direction, the first direction being a direction in which the plates are compressed; and releasing a compression of the plates on the tube at a rate of 50% of the initial distance of the two parallel plates per minute.

Embodiment 32: The tube of Embodiment 30 or 31, wherein a total energy value under an engineering stress-strain curve corresponding to the tube after the first compression is at least 138 kgf·mm/cm.

Embodiment 33: The tube of any preceding embodiment, wherein the tube has one or more of a therapeutic, a covering, and a coating applied thereon.

Embodiment 34: A tube, wherein: the tube comprises at least one crystallizable biodegradable polymeric material, and an outer surface that has a normal that is perpendicular to a length of the tube, the tube exhibits a maximum stress value of about 20 MPa or greater measured based on a first compression cycle; and a total energy value under an engineering stress-strain curve corresponding to the tube after the first compression is at least 138 kgf·mm/cm.

These and other features, aspects, and advantages of the disclosure will be apparent from a reading of the following detailed description together with the accompanying drawings, which are briefly described below. The invention includes any combination of two, three, four, or more of the above-noted embodiments as well as combinations of any two, three, four, or more features or elements set forth in this disclosure, regardless of whether such features or elements are expressly combined in a specific embodiment description herein. This disclosure is intended to be read holistically such that any separable features or elements of the disclosed invention, in any of its various aspects and embodiments, should be viewed as intended to be combinable unless the context clearly dictates otherwise. Other aspects and advantages of the present invention will become apparent from the following.

BRIEF DESCRIPTION OF THE DRAWINGS

In order to provide an understanding of embodiments of the invention, reference is made to the appended drawings, which are not necessarily drawn to scale, and in which reference numerals refer to components of exemplary embodiments of the invention. The drawings are exemplary only, and should not be construed as limiting the invention.

FIGS. 3A-3C are schematic depictions of different techniques for wrapping polymer films to form polymeric tubes;

DETAILED DESCRIPTION OF THE INVENTION

The present invention will now be described more fully hereinafter with reference to the accompanying figures, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

The disclosure relates to methods to produce polymeric tubes (e.g., biodegradable polymeric tubes) and to polymeric tubes produced thereby. In particular, the disclosure relates to methods to produce polymeric tubes comprising a crystallizable polymer, involving a molecular orientation step to align/orient at least some of the molecules of the crystallizable polymer within the walls of the tube (giving an oriented polymeric tube). In various embodiments, the methods disclosed herein provide control over crystalline molecular orientation within the polymeric tube walls, e.g., with respect to all three axes of a cylindrical coordinate system. The methods disclosed herein, in certain embodiments, involve selecting a predetermined final tubular geometry and an associated predetermined molecular orientation profile and selecting materials and method steps accordingly, e.g., by positioning and forming one or more precursors so as to achieve the desired final tubular geometry and molecular orientation profile. The disclosed methods can advantageously provide oriented polymeric tubes exhibiting sufficient strength/resistance to radial compression to render them useful in a range of applications, e.g., including, but not limited to, biomedical applications. The disclosed methods can also advantageously provide oriented polymeric tubes exhibiting more controlled and improved heat shrinkable properties with respect to tubes (e.g., oriented polymer tubes) produced by traditional extrusion and annular expansion.

Figure 1:
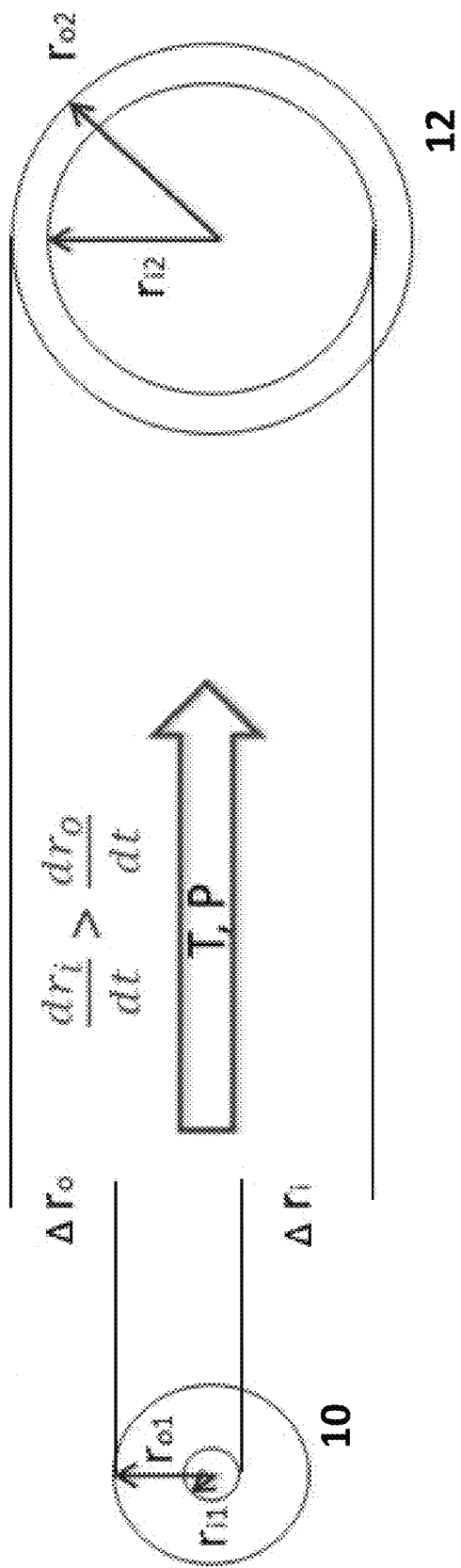
FIG. 1 is a background (prior art) schematic representation of the typical extrusion/expansion method for the production of single-layer oriented polymeric tubes.

As referenced above, traditional methods for the production of oriented polymeric tubes involve extrusion and annular expansion to provide single-layer tubes. In such methods, a polymeric tube is extruded by conventional methods and then is subjected to annular expansion, as shown schematically in FIG. 1 (prior art). As shown in FIG. 1, the extruded tube 10 is produced with a given inner diameter (ID), which is related to the inner radius (shown as $r_{i1}$) via the equation OD=2×$r_{i1}$, and a given outer diameter (OD), which is related to the outer radius (shown as $r_{o1}$) by the equation OD=2×$r_{o1}$. The extruded tube 10 is expanded (optionally under conditions of heat and pressure, as designated by T and P, respectively) to produce polymeric tube 12, with a larger ID (related to $r_{i2}$ based on the equation above) and a larger OD (related to $r_{o2}$ based on the equation above). With such expansion processes, the degree of stretching to which the ID of the extruded tube is subjected is greater than that to which the OD of the extruded tube is subjected. The differential in expansion rate and amount experienced by the ID and OD in such processes leads to an imbalance in the degree of molecular orientation through the tube wall (i.e., from the ID to the OD). As described above, typical annular expansion processes are limited as to the degree of orientation throughout the final wall thickness, resulting in a decreasing orientation gradient from the ID to the OD.

According to the present disclosure, various methods are provided for producing oriented polymeric tubes comprising a crystallizable polymer (e.g., a biodegradable crystallizable polymer, providing a resulting biodegradable oriented polymeric tube). In some embodiments, such tubes can exhibit modified molecular orientation properties and corresponding modified mechanical and/or thermodynamic properties with respect to oriented polymer tubes produced by traditional extrusion and annular expansion. Modified molecular orientation properties in this regard can mean a greater percentage of molecular orientation in crystalline regions of the oriented polymeric tube and/or greater regularity in the distribution of molecular orientation within crystalline regions of the oriented polymeric tube. For example, in some embodiments, the molecular orientation throughout the thickness of a wall of the disclosed oriented polymeric tube is more uniform than that of a wall of an oriented polymeric tube produced by conventional methods as shown in FIG. 1 (leading to such improved mechanical and thermodynamic properties). Modified mechanical properties can mean higher strength, higher modulus, higher toughness, and/or greater elasticity. Modified thermodynamic properties can mean modified heat shrinkable properties, including, but not limited to, controlled shrinkage activation temperature, shrinkage force, and shrinkage ratios.

Planar Orientation and Annular Positioning

One method provided herein involves use of uniaxially or biaxially oriented polymeric films as oriented precursors for the formation of oriented polymeric tubes (referred to herein as "planar orientation and annular positioning"). Orienting polymer molecules by stretching them into uniaxially or biaxially oriented films is known to improve properties such as tensile strength and toughness. See, e.g., "Understanding biaxially and monoaxially oriented films", *Packaging World*, Oct. 20, 2013.

Figure 2:
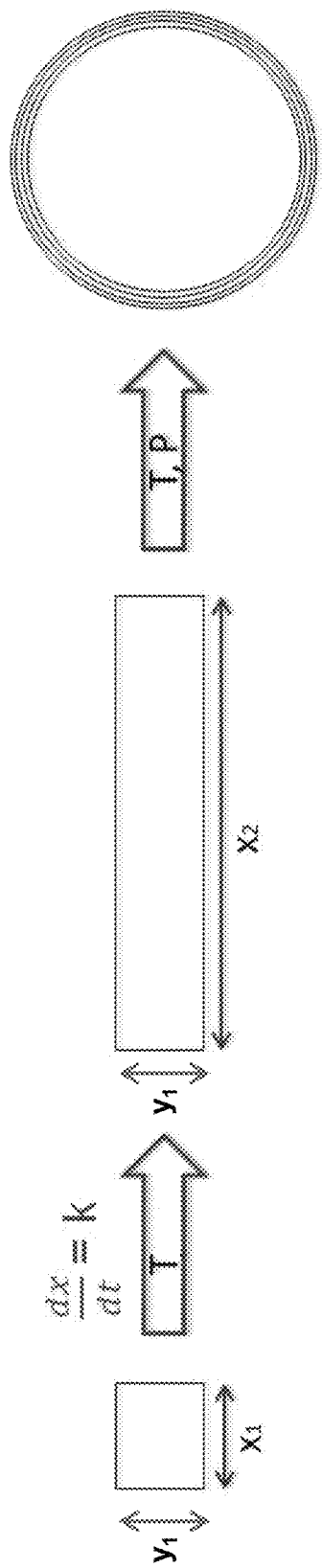
FIG. 2 is a schematic representation of a method disclosed herein for the production of oriented polymeric tubes via planar orientation and annular positioning.

One embodiment of the presently disclosed method is shown schematically in FIG. 2. According to this method, a polymer film comprising a crystallizable polymer, having a given dimension $x_1$ (considered here to be the film length), is stretched in the planar direction to give a stretched polymer film with corresponding dimension $x_2$, which is larger than $x_1$ (i.e., the stretched polymer film is increased in length). The stretched polymer film is referred to herein as an "oriented" polymer film, as the stretching process imparts at least some degree of molecular orientation within crystalline regions of the polymer film.

The polymer film can be of varying sizes and thicknesses, and the amount of stretching (related to $x_1$ and $x_2$ values) can, in some embodiments, be determined based on the desired thickness (z, not shown in FIG. 2) of the stretched/oriented film relative to the initial thickness of the (unstretched/unoriented) film. In some embodiments, the amount of stretching (related to $x_1$ and $x_2$ values) can be determined based on the desired mechanical and/or thermodynamic properties of the stretched/oriented film. The embodiment depicted in FIG. 2 provides for uniaxial stretching (stretching/increasing dimension x only); however, in some embodiments, the disclosed method involves biaxial stretching (stretching/increasing both dimensions x and y, i.e., length and width). In such embodiments, the stretching rates and/or amounts in both the x and y directions can be modified independent of each other. Planar stretching (in either one dimension only, i.e., uniaxially, or in two dimensions, i.e., biaxially) is advantageously done in a controlled manner, such that the stretch rate, denoted by "k," i.e., dx/dt (FIG. 2) is constant and the resulting stretched/oriented polymer film is substantially homogeneous (e.g., in terms of thickness). Where the planar stretching is uniaxial, as shown in FIG. 2, it is understood that the stretch rate for the other axis (here, along the y axis), dy/dt is equal to 0 (i.e., there is no stretching along the y axis). One of skill in the art would recognize that dy/dt is non-zero where there is stretching along the y axis.

The polymer film subjected to stretching can be produced by any of a number of methods, including, but not limited to, extrusion, extrusion coating, injection/blow molding, melt casting, solvent casting, or compression molding (the latter two processes allowing for the use of higher molecular weight polymers than extrusion). In some embodiments, materials such as fillers can be dispersed into the polymer film prior to the stretching step. In certain embodiments, a tie layer material is associated with the polymer film prior to stretching (such that both the polymer film and the tie layer material are stretched together), as will be described in further detail below. It is noted that, although the application is described specifically in the context of polymer films that are stretched (and, as referenced below, polymer profiles), the disclosure is not intended to be limited thereto. For example, in other embodiments, a polymeric material in the form of a polymer monofilament, a polymer ribbon, a polymer tape, or a polymer rod is used. One of skill in the art is familiar with these terms and will appreciate, e.g., that a polymer monofilament is a threadlike synthetic fiber (which fibers can have varying diameters), a polymer tape is a flattened strip of polymeric material (which tapes may have varying lengths and widths), and a polymer rod is a three-dimensional structure (although not limited to being circular in diameter). As an example, a polymer rod can be a cylindrical structure. As another example, a polymer rod can be a tubular structure.

There are a number of methods known in the art to stretch a polymeric material in one or two dimensions as described above. In machine direction (MD) stretching, an extruded film is cast onto a chill roll then reheated and passed through a nip and over tensioning rollers at speeds exceeding the extrusion casting speed to stretch the material. A subsequent transverse direction (TD) stretching can be accomplished by gripping the sides of the film in clamps and pulling the clamps normal to the machine direction through a heated oven in a tenter frame. Alternatively, the MD and TD stretching can be accomplished simultaneously in a tenter frame capable of simultaneous biaxial orientation, such as a LISIM line manufactured by Brückner. The line speeds, temperatures and stretching rates are controlled to achieve the desired extent of stretching without tearing the film. Simultaneous stretching of the polymeric material can also be achieved by using a blown film line which extrudes the polymeric material through an annular die and then inflates the extrudate with air to create a bubble which serves to stretch the material in both TD and MD directions. If additional MD or TD stretch is required, the blown film line can be modified to provide a second bubble to achieve higher extents of stretching in either or both MD and TD. There are many manufacturers of industrial blown film and double-bubble lines, such as Hosokawa Alpine, GAP srl. or Kuhne Group. In addition to the continuous processes herein outlined, batch-wise stretching can be achieved, in some embodiments, by clamping a polymeric film on all sides and stretching it in an oven in one or both of MD and TD sequentially or simultaneously. The Karo IV stretcher manufactured by Brückner provides one example of a batch-wise film stretcher.

The degree to which the polymer film is stretched can vary, as referenced above. In some embodiments, the polymer film is stretched at least ten percent of a maximum stretch ratio respectively corresponding to the at least one polymeric material. "Maximum stretch ratio" as used herein is intended to mean the maximum stretch possible before tearing of the material occurs.

Using the stretched, oriented polymer film as a precursor for the formation of a tubular form, the stretched, oriented polymer film is positioned in an annular configuration (e.g., by rolling or wrapping the stretched, oriented polymer film) and optionally further processed to provide the oriented polymeric tube (e.g., the oriented biodegradable polymeric tube). Although the present disclosure focuses on positioning the stretched, oriented polymer film in an annular configuration by rolling/wrapping the film to provide a tubular form, other means for positioning are also encompassed herein.

The stretched, oriented polymer film may optionally be further processed prior to this step, e.g., by cutting the film into individual desired sizes and/or by associating a tie layer therewith, as will be described in further detail below. Although not intended to be limiting, one means for positioning the stretched, oriented polymer film in an annular configuration comprises wrapping/rolling the film around a forming mandrel. It is noted that the shape of the forming mandrel is not particularly limited. As such, a polymeric "tube" as used herein is understood to not be limited to cylindrical tubes. Rather, a polymeric "tube" produced according to the disclosed methods is any hollow, elongated structure, wherein the cross-sectional shape of the hollow, elongated structure may be, but is not limited to, being round.

The disclosed method further is not limited to wrapping/rolling the film around a mandrel; rather, the film can be wrapped around various types of supports. Suitable supports include, but are not limited to, supports with one or more of a cylindrical shape, a round shape, a rectangular shape, a triangular shape, an elliptical shape, a polygonal shape, and a tubular form. In some embodiments, the support is a device or device component (e.g., including, but not limited to, a stent). In certain such embodiments, the method disclosed herein provides a composite comprising the support and the positioned oriented polymer film, which can be in the form of a medical device. Particularly where the support is a device and where the disclosed method provides a medical device, the composite can, in some embodiments, be further processed. For example, in some embodiments, one or more of a therapeutic, a covering, and a coating is applied to the composite. In some embodiments, the composite is cut into appropriate sizes for stents. Various methods are known for cutting stents, including, but not limited to, laser cutting.

The oriented polymer film can, in some embodiments, be positioned by rolling/wrapping as described above to provide a single-layer oriented polymeric tube with little to no overlap of one edge of the polymer film with the opposite edge of the film (e.g., with only a small seam where the two film ends meet) or by rolling/wrapping the film multiple times to produce a multi-layer tube. More preferably, a multi-layer tube (e.g., a tube with a "layered structure") is formed, having any number of layers, wherein the number of layers is not particularly limited. Exemplary such multi-layer tubes have 2 to 20 layers of the oriented polymer film, which preferably comprises a single oriented polymer film wrapped/rolled so as to give the desired number of layers (e.g., to achieve the desired wall thickness of the resulting multi-layer oriented polymeric tube). It is understood that, in such embodiments, a greater number of layers/wrappings will provide a polymeric tube with thicker walls (assuming an oriented polymer film with the same thickness is used). As such, the number of layers/wrappings can dictate the wall thickness of the resulting oriented polymeric tube. The axis along which the polymer film is rolled/wrapped with respect to the axis/axes along which the polymer film has been stretched/oriented can vary, as shown in FIGS. 3A-3C. The circular arrow indicates the direction of wrapping.

Typically, to provide sufficient adhesion between layers of adjacent oriented polymer films of such multi-layer polymeric tubes (e.g., produced by positioning and forming multiple wrappings of one or more films), a tie layer (e.g., an "adhesive polymeric material") as described herein below is included within the oriented polymeric tube. In some embodiments, a tie layer is incorporated by associating a tie layer material with an (unstretched/unoriented) polymer film as described herein above to provide a composite polymer film, and subjecting this composite polymer film to planar expansion as described above. This associating can be done, e.g., by aligning a tie layer material film with the (unstretched/unoriented) polymer film or by coating the (unstretched/unoriented) polymer film with the tie layer material, such as by extrusion coating or solution-coating the tie layer material onto the polymer film. This method provides both the crystallizable polymer film and the tie layer in stretched form (and, in some such embodiments, this method could provide molecular orientation within not only the polymer film, but also within the tie layer).

In another embodiment, a tie layer is incorporated by associating a tie layer material with a stretched/oriented polymer film. In such embodiments, a composite film is provided by subjecting a crystallizable polymer film to stretching/orientation and subsequently associating a tie layer material with the stretched, oriented polymeric film. This associating can be done, e.g., by aligning a tie layer material film with the (stretched/oriented) polymer film or by coating the (stretched/oriented) polymer film with the tie layer material, such as by extrusion coating or solution-coating the tie layer material onto the polymer film. The composite polymer film provided according to this embodiment comprises the crystallizable polymer film in stretched/oriented form, while the tie layer is in unstretched/unoriented form. Other modifications to these embodiments are also encompassed, e.g., wherein a polymer film and tie layer are independently stretched to give a stretched/oriented polymer film and a stretched or stretched/oriented tie layer, which can be combined to give a composite polymer film.

As briefly noted herein above, the composition of the oriented polymer film(s) and the composition of the tie layer(s) can be the same or different. As such, in certain embodiments, the composition of one or more of the oriented polymeric films is the same as the composition of one or more tie layers, but the polymers are oriented to different extents (e.g., the oriented polymeric film(s) are oriented to a greater degree than the tie layer(s)).

The composite polymer film is then formed into an oriented polymeric tube as provided herein above, such that the tie layer material is associated with each "layer" (or wrap) of the oriented polymer film and bonds adjacent layers of the polymeric film together. The bonding may, in some embodiments, require treatment of the polymeric tube by subjecting the final polymeric tube to heat and/or pressure. In some embodiments, the pressure is negative pressure, i.e., application of vacuum to the tube, such as by pulling a vacuum through a mandrel around which the polymeric tube is wrapped. In some embodiments, heat and (positive) pressure are provided by wrapping the polymeric tube in a shrink material (e.g., a shrink tube or shrink wrap comprising linear low-density polyethylene, LLDPE) and heating the wrapped polymeric tube (e.g., by placing the tube in an oven). The oven temperature, forming time, and the forming pressure applied can depend on the components of the polymeric tube and these processing variables can each be controlled to tune the final oriented polymeric tube properties. In some embodiments, other bonding techniques can be employed, to replace or supplement the heat/pressure method. For example, in some embodiments, bonding can employ contact with one or more solvents (e.g., chloroform) and in some embodiments, bonding can involve the use of radiofrequency welding.

Although the planar orientation/annular positioning methods outlined herein above are disclosed as comprising three distinct steps (planar orientation, e.g., stretching a polymer film, annular positioning, e.g., positioning the oriented polymer film in an annular position, and forming, e.g., forming the positioned oriented polymer film into an oriented polymeric tube), the disclosed method can be modified so as to conduct two or all three of these steps largely simultaneously. For example, in some embodiments, a polymer film may be provided in unstretched form and can be stretched (and oriented) by air and/or liquid pressure against a cylindrical forming surface to form an oriented polymeric tube.

In some embodiments, rather than utilizing a stretched polymer film as the polymeric tube precursor, an oriented composite polymer profile is positioned and formed into a tube and thus can serve as the polymeric tube precursor. This method involves positioning the oriented composite polymer profile with respect to all three cylindrical axes according to a desired orientation profile. The positioning of the composite profile can include, but is not limited to, wrapping, sheathing, winding, or braiding. This positioned composite profile is subjected to pressure and/or temperature such that the tie layer(s) adhere to adjacent layers of the composite profile, thereby forming a coherent, multi-layer oriented polymeric tube.

A polymer profile is a shaped polymeric form (rather than a polymer film as referenced above), which comprises a crystallizable polymer as disclosed herein. Exemplary polymer profiles include, but are not limited to, cross-sectional profiles in the form of squares, rectangles, polygons, ellipses, or other geometric shapes that may or may not possess regular or intermittent features on one or more surfaces of the shape. A composite profile is a polymer profile (comprising a crystallizable polymer as referenced above), further comprising a tie layer material.

In certain embodiments, tubes produced by positioning and forming oriented films or profiles as outlined in this section exhibit a more consistent degree of molecular orientation across the tube wall thickness than that across the tube wall thickness of an extruded and radially expanded single-layer tube (produced as referenced above and as shown schematically in FIG. 1). Using a cylindrical coordinate system and assuming two surfaces in full contact (excluding tie layers of negligible thickness) are geometrically continuous, such a tube formed from a round-shaped profile positioned to give maximum density will be geometrically discontinuous along all three axes. With respect to molecular orientation and imposing geometrical continuity, such a tube would be continuous along the θ-axis and discontinuous along the r-axis and z-axis. Such a tube formed from a rectangular-shaped profile positioned to give maximum density will be geometrically discontinuous along all three axes. With respect to molecular orientation and imposing geometrical continuity, such a tube would be continuous along all three axes.

The planar orientation/annular positioning method disclosed herein provides a number of advantages as compared to traditional extrusion/annular expansion. For example, according to the disclosed method, each polymer film (or profile) can be stretched uniaxially or biaxially as desired, to the degree desired. Multiple polymers can, in some embodiments, be combined as individual layers in a composite structure and stretched (and oriented) together. In some embodiments, multiple polymers can be independently provided in film or profile form and stretched (and oriented) to different extents and then these oriented films and/or profiles can be combined before or during the forming of the polymeric tube.

Figure 4B:
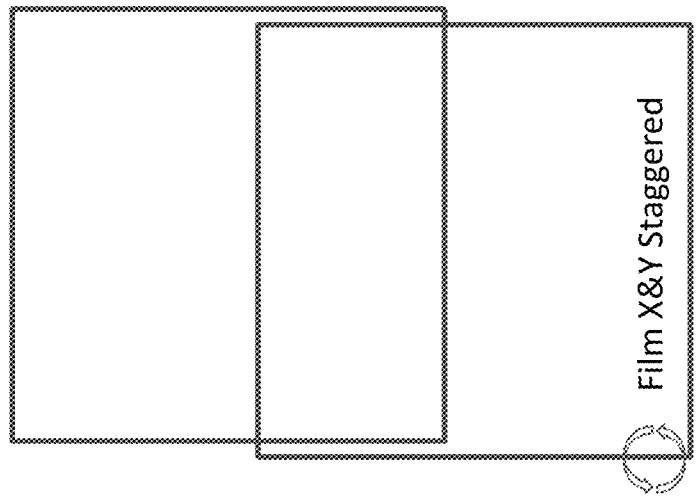
FIGS. 4A and 4B are schematic depictions of methods of aligning adjacent polymer films to form polymeric tubes.
Figure 4A:
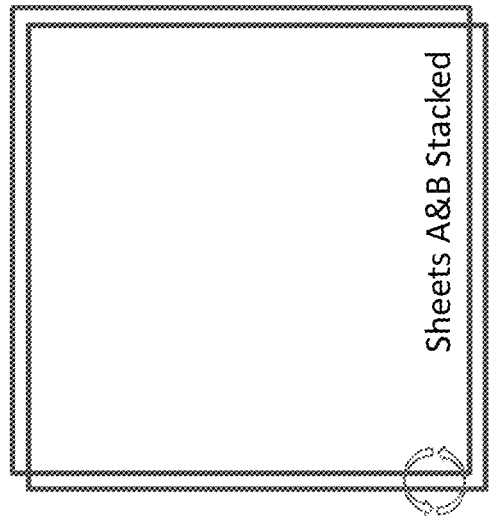

The manner in which different polymer films (or profiles) can be combined may be varied to achieve different composite structures and different properties. For example, in some embodiments, multiple films can be plied up on a bias angle during the tube forming process (e.g., at the forming mandrel) to match critical application requirements. Various configurations of the component layers can be obtained during production. For example, individual layers may be staggered or stacked with respect to one another. In this context, stacked configurations (e.g., as shown in FIG. 4A) comprise different films directly on top of each other and staggered configurations (e.g., as shown in FIG. 4B) comprise different films offset such that when they are rolled (or otherwise formed into tubular form), the initial layer(s) is a single material followed by one or more layer(s) of a composite film (or profile), followed by one or more layers of the final material. A given oriented polymer tube could further be provided with a stacked set of layers and a staggered set of layers.

In some embodiments, individual films/layers can be selected for very specific properties such as strength, toughness, inclusion/elution of drugs, adhesion, surface functionality, degradability, etc., to afford such properties to the resulting polymeric tube. Additional components can be incorporated within the final tube at various stages of the production method outlined herein (e.g., between films that are subsequently encapsulated by the tie layer(s) prior to or during the forming step), including, but not limited to, braids, fibers, wovens, nonwovens, and/or inserts. In some embodiments, oriented polymeric tubes provided via the method disclosed herein can be further altered in subsequent steps to produce a medical device (e.g., by laser cutting, crimping, expansion, etc.).

Multilayer Annular Orientation and Annular Positioning

Another aspect of the present disclosure relates to methods involving multilayer annular orientation and annular positioning and to oriented polymeric tubes produced thereby. As described above, one disadvantage of an annular expansion process is that the degree of orientation throughout the final tube wall thickness is limited, resulting in a decreasing orientation gradient from the ID to the OD. This concern can be addressed by employing an annular orientation approach, but minimizing the wall thicknesses, as the limitation on degree of orientation achievable approaches zero as the wall thickness approaches zero. Therefore multilayer tubes formed from annularly oriented tube precursors where the wall thicknesses of the precursors become additive in the formation of the wall thickness of the final formed oriented polymeric tube, will exhibit a higher degree of orientation throughout the tube wall thickness and a reduced orientation gradient from the ID to the OD of the final formed polymeric tube.

Figure 5A:
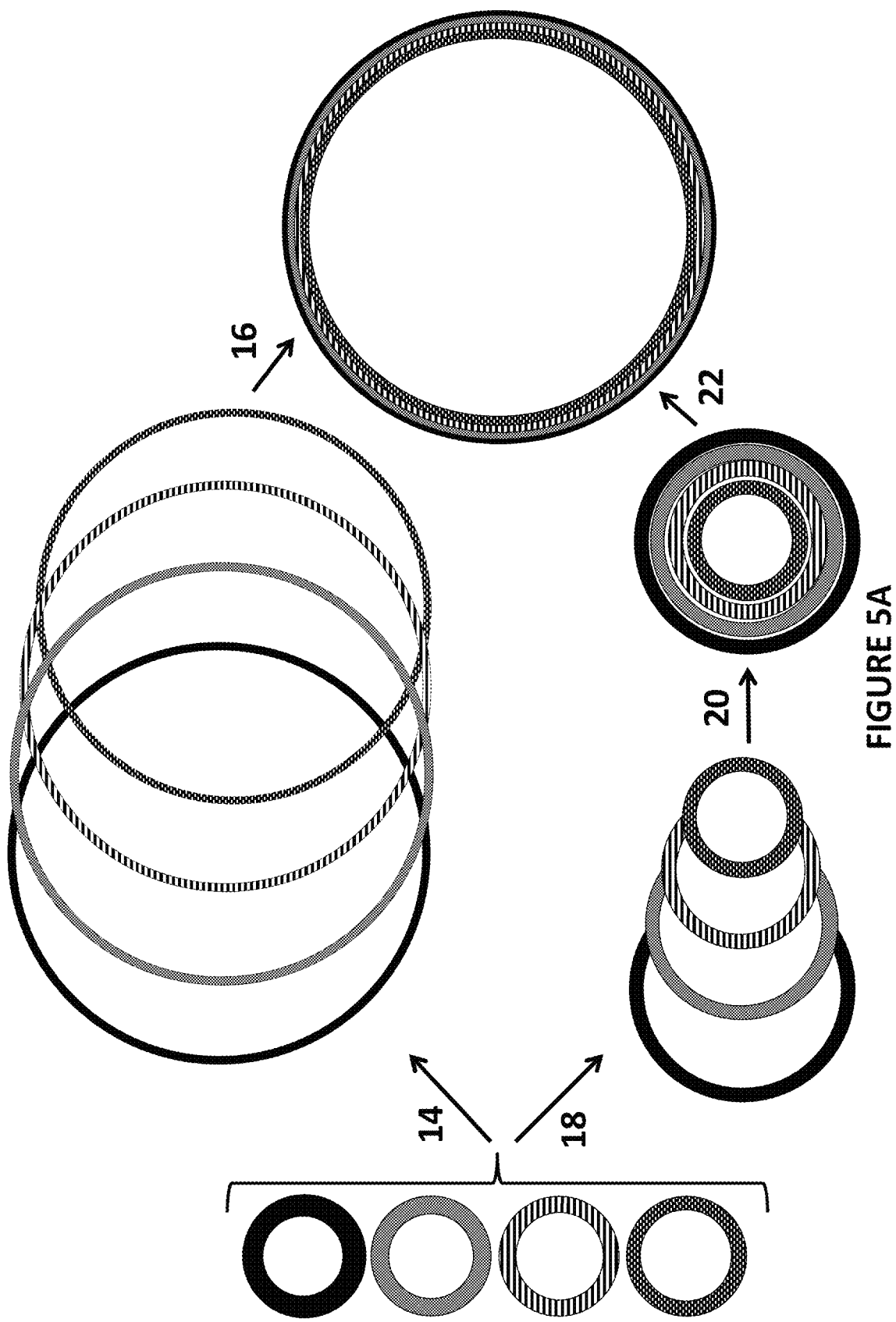
FIGS. 5A and 5B are schematic representations of certain methods disclosed herein for the production of oriented polymeric tubes via multilayer annular orientation and annular positioning.

In this multilayer annular orientation and annular positioning approach, multiple polymeric tubes (which can be of the same composition or different compositions) are prepared and subjected to annular expansion, thereby producing oriented tube precursors with at least some degree of molecular orientation, as shown in FIG. 5A (step 14 or 18). Such polymeric tubes can be made by any method, e.g., via extrusion, extrusion coating, and/or injection molding. In one embodiment, the individual oriented tube precursors are positioned in a nested manner as shown in step 16. In another embodiment, oriented tube precursors are positioned in a nested manner as shown in step 20, and then subjected to additional annular expansion (simultaneously) as shown in step 22. The positioning of the oriented tube precursors in such embodiments is completed via the annular expansion step. The formation of the final tubular geometry (giving an oriented multilayer polymeric tube) can be completed via the annular expansion step or subsequent to the annular expansion step.

Figure 5B:
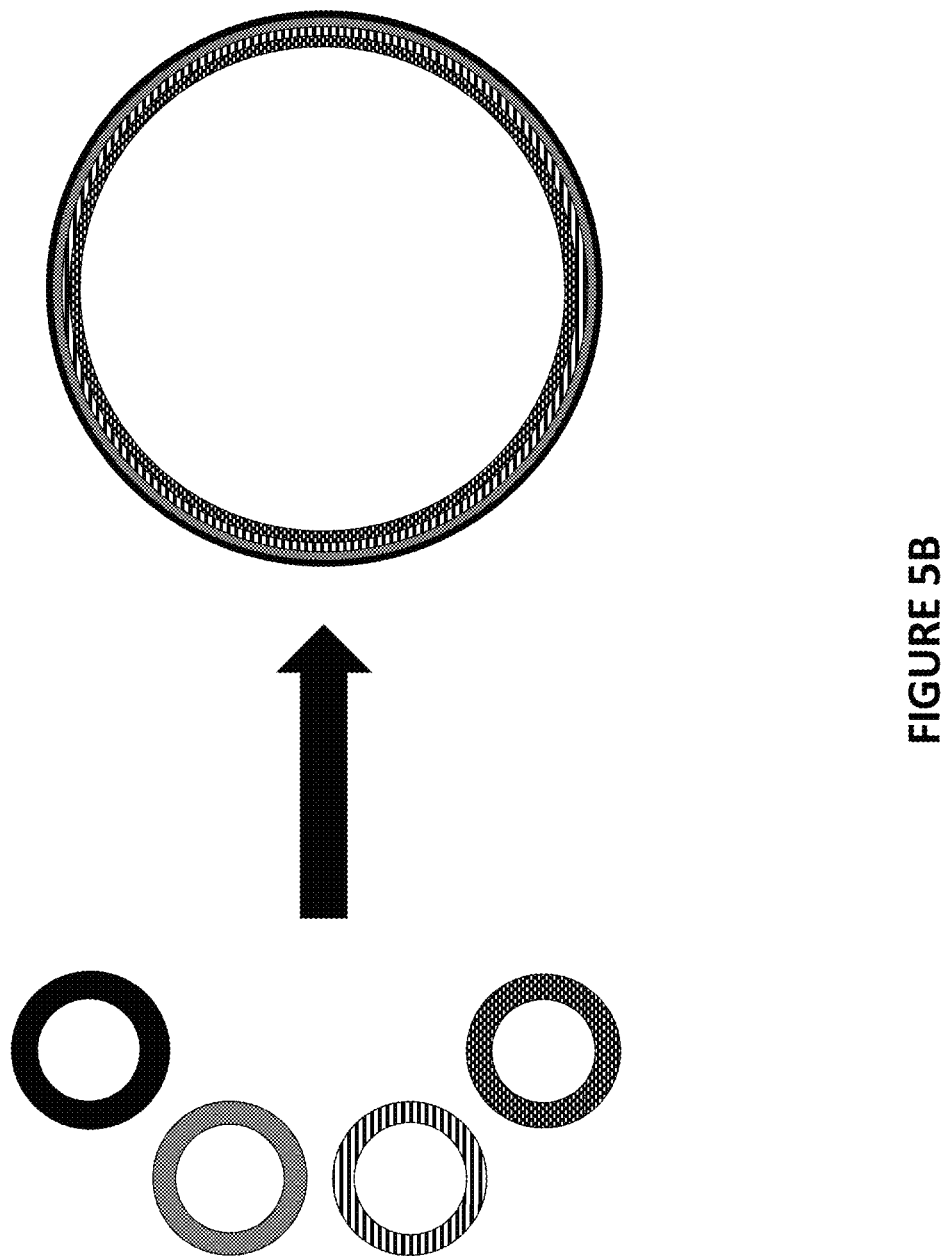

In another embodiment, the annular expansion of the polymeric tubes can take place sequentially, one within another, as shown in FIG. 5B. Following the annular expansion of the first tube (making up the outer oriented tube precursor), the annular expansion of each subsequent tube positions an additional oriented tube precursor within the ID of the preceding oriented tube precursor, resulting in the annular positioning of all oriented tube precursors. The formation of the final tubular geometry (giving an oriented multilayer polymeric tube) can be completed via the annular expansion of one or more tube precursors or subsequent to the annular expansion of one or more tube precursors. The annular expansion for any of these embodiments can be conducted by any known method for expanding tubes annularly.

Combining multiple unstretched/unoriented polymeric tube precursors or stretched/oriented tube precursors using this method can be conducted in various ways, e.g., by forming the oriented polymeric tube on a mandrel (optionally with the application of heat and/or pressure) or by forming the oriented polymeric tube within a mold (again, optionally with the application of heat and/or pressure). It is noted that such forming mandrels and molds are not required to be round in cross section, and as such, the resulting multi-layer oriented polymeric tube can be in the form of a hollow, elongated structure that can be, but is not limited to, being round in cross-section.

With the multilayer annular orientation and annular positioning method, due to the inclusion of multiple individual layers, a tie layer is again typically incorporated between adjacent layers to provide sufficient adhesion there between. In these embodiments, the inclusion of a tie layer can be achieved, for example, by associating a tie layer material with one or more polymeric tube precursors (to provide composite polymeric tube precursors), such that when the polymeric tube precursor is expanded/oriented and combined with other precursors (or combined with other precursors and then expanded/oriented), the tie layer is similarly subjected to such processes as well. As such, in some embodiments, the tie layer is similarly subjected to annular expansion/orientation. In other embodiments, the tie layer is applied after the individual polymer tubes have been expanded/oriented and in such embodiments, the tie layer is not subjected to annular expansion/orientation. Again, forming the final oriented polymer tube by bonding adjacent layers (arising from the combining of multiple tube precursors or multiple individually expanded/oriented tubes) may require treatment of the final oriented polymeric tube by subjecting the multi-layer oriented polymeric tube to heat and/or pressure. In some embodiments, heat and pressure are provided by wrapping the oriented polymeric tube in a shrink tube or shrink wrap and heating, e.g., by placing the wrapped oriented polymeric tube in an oven. The oven temperature and the forming pressure applied can each be controlled to tune the final tube properties.

As such, in certain embodiments (e.g., as depicted by steps 16 and 22 in FIG. 5A), at least two oriented tubes (which each can comprise one crystallizable polymeric layer and, optionally, one tie layer (giving a composite oriented tube)) are positioned with respect to all three cylindrical axes according to a desired orientation profile. The positioned tubes are subjected to increased pressure and/or temperature such that the tie layer adheres to adjacent layers (i.e., the oriented polymer layers on either side thereof), thereby forming a coherent multilayer oriented polymeric tube. In some embodiments, a composite stretched, oriented tube is positioned with respect to an outer and/or inner expanded/oriented tube comprising a crystallizable polymer (which may or may not comprise a tie layer).

In some embodiments (e.g., as depicted in FIG. 5B), non-oriented composite tubes (comprising both the crystallizable polymer and a tie layer material) are expanded annularly (e.g., under conditions of elevated temperature and pressure), orienting at least a portion of the crystallizable polymer. Via this annular expansion process, the tie layer material can, in some embodiments, adhere to any adjacent layers. For example, in this embodiment, one adjacent layer is the crystallizable polymer of the same non-oriented composite tube precursor and the other adjacent layer can be an already oriented tube of a second crystallizable polymer (which may be the same as or different than the crystallizable polymer in the composite tube precursor), thereby forming a coherent multi-layer oriented polymeric tube. In such embodiments, the individual layers are positioned with respect to all three cylindrical axes according to a desired orientation profile. The composite tube precursor can also be positioned with respect to an inner tube precursor comprising the crystallizable polymer.

There are a number of methods known in the art to annularly expand polymeric tubes as described above. In conventional blow molding, an extruded polymeric tube is disposed within a mold, heated to a rubbery state, and pressurized to expand the tube into the mold. In some methods, the extruded polymeric tube is also stretched in the machine direction by applying tension. The machine direction stretching is completed prior to or during the annular expansion. The final expanded tube geometry is generally determined by the geometry of the mold and the process parameters such as temperature and pressure. The properties of the final expanded tube are generally determined by process parameters such as annular expansion ratio, annular expansion rate, machine direction stretch ratio, machine direction stretch rate, temperature, and pressure.

The multilayer annular orientation and annular positioning method disclosed herein provides a number of advantages as compared to traditional extrusion/annular extrusion. For example, each tube precursor can be oriented uniaxially or biaxially as desired, to the degree desired prior to or during the formation of the multi-layer oriented polymeric tube, to match application requirements. Multiple polymers can, in some embodiments, be combined as individual layers in a composite structure and expanded/oriented together. In some embodiments, multiple polymers can be independently provided in tube form and expanded (and thus oriented), e.g., to different extents and then the resulting oriented tubes can be combined during positioning and forming of the multi-layer oriented polymeric tube. In some embodiments, individual tubes and tube precursors can be selected for very specific properties such as strength, toughness, inclusion/elution of drugs, adhesion, surface functionality, degradability, etc., to afford such properties to the resulting multi-layer polymeric tube. Additional components, e.g., fillers can be dispersed in one or more of the tube precursors prior to expansion. Additional components can be incorporated within the final multi-layer polymeric tube at various stages of the production method outlined herein (e.g., between tubing layers that are subsequently encapsulated by the tie layer(s) materials), including, but not limited to, braids, fibers, wovens, nonwovens, and/or inserts. In some embodiments, the multilayer polymeric tube provided via the method disclosed herein can be further altered in subsequent steps to produce a medical device (i.e., by laser cutting, crimping, expansion, etc.).

Using the cylindrical coordinate system and assuming two surfaces in full contact are geometrically continuous, such tubes (formed from precursor annular geometries) will be geometrically continuous along all three axes. With respect to molecular orientation and imposing geometrical continuity, such a tube would be continuous along the z-axis and the θ-axis and discontinuous along the r-axis.

The oriented polymeric tube production methods disclosed herein are applicable to a range of crystallizable polymers. Such methods are particularly applicable to biodegradable polymers (although not limited thereto). As such, in preferred embodiments, the polymer(s) from which oriented polymeric tubes are prepared according to the present disclosure are advantageously crystallizable biodegradable polymers and advantageously are capable of exhibiting high molecular orientation, strain-induced crystallization, and high strength.

Biodegradable (also commonly referred to as "bioabsorbable" and/or "bioresorbable") polymers are those polymers that will, under certain biological conditions, undergo breakdown or decomposition into compounds considered to be harmless/safe as part of a normal biological process. Advantageously, under the biological conditions to which they are subjected, biodegradable polymers gradually degrade and/or erode and are absorbed or resorbed within the body. Typically, biodegradable polymers applicable in the context of the present disclosure are sufficiently stable under biological conditions to remain in the body for a duration of time (e.g., including, but not limited to, up to about 1 week, up to about 1 month, up to about 3 months, up to about 6 months, up to about 12 months, up to about 18 months, up to about 2 years, or longer) before substantial degradation. Typically, such biodegradable polymers are also biocompatible.

Exemplary crystallizable polymers applicable in the context of the present invention include, but are not limited to, poly(L-lactide) (PLLA), poly(D-lactide) (PDLA), poly(ε-caprolactone) (PCL), polyglycolic acid (PGA), poly(para-dioxanone) (PDO), poly(hydroxybutyrate), poly(hydroxyvalerate), poly(tetramethyl carbonate), poly(ethylene oxide) (PEO), poly(ethylene glycol) (PEG), poly(propylene glycol), polydioxanone, polygluconate, and copolymers, blends, and derivatives thereof. Certain polymers that can be used according to the disclosed methods can be characterized as poly(alpha-hydroxy acids). Some polymers are modified cellulosic polymers, collagen or other connective proteins, adhesive proteins, hyaluronic acid, polyanhydrides, polyphosphoesters, poly(amino acids), and copolymers and derivatives thereof. The molecular weight of the polymers processed according to the methods outlined herein can vary and may affect the properties of the resulting oriented polymeric tubes. It is generally understood that mechanical properties of polymers (e.g., strength and modulus) generally improve with increasing molecular weight and that degradation time generally increases with increasing molecular weight (i.e., a tube made of a low molecular weight polymer typically degrades more quickly than a comparable tube made of a higher molecular weight polymer). As such, polymer molecular weights can be selected accordingly to balance these properties, and may vary widely, depending on the particular application.

As described above, the oriented polymeric tubes disclosed herein commonly comprise, in addition to the oriented crystallizable polymer, one or more tie layer materials (also referred to herein as "adhesive" layer materials) sufficient to bind multiple layers together. Such multiple layers can comprise multiple layers of the same material (e.g., in the case of a multi-layer material produced by wrapping) and/or can comprise layers of different materials. Advantageously, in some embodiments, the tie layer bonds adjacent layers together such that the oriented polymeric tube exhibits little to no delamination during use (e.g., the adhesion between layers allows for the oriented polymeric tube to undergo at least partial degradation without exhibiting sufficient delamination).

The composition of the tie layer(s) within the final oriented polymeric tube can vary. Tie layers typically comprise one or more polymers capable of bonding two adjacent layers together and as such, various polymers with adhesive properties may be used. Typical adhesive polymers for use as tie layers exhibit some degree of flow and/or tackiness. The polymer(s) comprising the tie layers, in some embodiments (e.g., where the final product is designed for implantation within the body) are preferably biocompatible, biodegradable polymers. The polymer(s) comprising the tie layers, in some embodiments, are non-crystalline/substantially amorphous polymer(s). Exemplary polymers that are suitable to serve as (or be included within) tie layers according to the present disclosure include, but are not limited to, poly(ε-caprolactone), poly(trimethylene carbonate), poly(D,L-Lactide), poly(L-Lactide)-co-ε-caprolactone), poly(L-Lactide-co-trimethylene carbonate, poly(ε-caprolactone-co-trimethylene carbonate), poly(ethylene glycol), poly(L-lactide-co-poly(ethylene glycol)), and copolymers and derivatives and combinations thereof.

The properties of tubes produced by the foregoing methods can vary. For example, the geometric continuity and orientation continuity of oriented polymeric tubes prepared by the various methods are compared below in Table 1.

TABLE 1

Geometric/orientation continuities for tubes prepared according to disclosed methods

| | Geometric Continuity | | | Orientation Continuity | | |
|---|---|---|---|---|---|---|
| | z-axis | r-axis | Θ-axis | z-axis | r-axis | Θ-axis |
| Rolled Film(s) | x | — | — | x | x | x |
| Wound Round Profile | — | — | — | — | — | x |
| Wound Rectangular Profile | — | — | — | x | x | x |
| Multilayer Annular Tubes | x | x | x | x | — | x |

The shapes and sizes of oriented polymeric tubes produced according to the disclosed methods can vary. As noted herein above, such tubes may be cylindrical, but are not limited thereto. Wall thicknesses of the oriented polymeric tubes can vary as well and can be tailored based on, e.g., the polymer film (or profile) thickness (for the planar orientation and annular positioning method), tube/tube precursor thickness (for the multi-layer annular orientation and annular positioning method), the amount of elongation force applied thereto, and the number of layers combined to produce the final oriented polymeric tube (e.g., the number of wrappings or the number of tube precursors or tubes combined to produce a multi-layer tube). Oriented polymeric tubes provided according to the present disclosure can be substantially homogeneous in composition (e.g., consisting primarily of a single oriented crystallizable polymer component), wherein multiple layers thereof may be bonded together with a comparatively small amount of tie layer material (forming an adhesive/tie layer between adjacent layers of the oriented polymer. Certain oriented polymeric tubes provided according to the present disclosure can be non-homogenous, as films/profiles/tubes can be combined which are compositionally different (e.g., tubes may comprise different crystallizable polymers and/or different tie layer materials (which may be stretched or may be in unstretched form), may include/exclude fillers or other components, etc.). The methods outlined herein are broadly applicable to the preparation of a wide range of oriented polymeric tubes.

In some embodiments, oriented polymeric tubes prepared according to the disclosed methods can be characterized by the degree of molecular orientation of the crystallizable polymer across a cross-section of the tube (i.e., from the ID to the OD of the tube). Preferably, the molecular orientation of the crystallizable polymer within the tube walls is substantially unchanged across the cross-section of the oriented polymeric tube. For example, the molecular orientation is generally in the same direction and is in about the same amount near the ID as near the OD of oriented polymeric tubes according to the present disclosure. Such orientation characteristics can be evaluated, e.g., using x-ray diffraction.

In particular, the molecular orientation profile in certain embodiments is substantially consistent through a wall of the oriented polymeric tube, or is substantially consistent through predefined portions of a wall of the oriented polymeric tube. In some embodiments, tubes have a molecular orientation profile characterized by varying levels of orientation through predefined portions of a wall of the oriented polymeric tube and/or characterized by varying axes of orientation through predefined portions of a wall of the oriented polymeric tube. Some tubes provided herein exhibit other profiles, e.g., an increasing molecular orientation gradient through a wall from the inner diameter to the outer diameter of the oriented polymeric tube or a decreasing molecular orientation gradient through a wall from the inner diameter to the outer diameter of the oriented polymeric tube. In some embodiments, the molecular orientation profile is substantially consistent along the length of the oriented polymeric tube or that is substantially consistent along predefined portions of a length of the oriented polymeric tube. In some embodiments, tubes have a molecular orientation profile characterized by varying levels of orientation along the length of the oriented polymeric tube and/or characterized by varying axes of orientation along the length of the oriented polymeric tube.

The compositional profile of an oriented polymeric tube as provided herein, in certain embodiments, is substantially consistent through a wall of the oriented polymeric tube or is substantially consistent through predefined portions of a wall of the oriented polymeric tube. In other embodiments, the composition profile can be characterized by varying compositions through predefined portions of a wall of the oriented polymeric tube. Similarly, the compositional profile of an oriented polymeric tube as provided herein, in certain embodiments, is substantially consistent along a length of the oriented polymeric tube or is substantially consistent along a length of the oriented polymeric tube. In other embodiments, the composition profile can be characterized by varying compositions along a length of the oriented polymeric tube.

In certain embodiments, the degradation rate profile can be affected by the specific methods used for formation of an oriented polymeric tube. For example, oriented polymeric tubes are provided herein which are characterized by a degradation rate profile that is substantially consistent through a wall of the oriented polymeric tube, characterized by a degradation rate profile that is substantially consistent through predefined portions of a wall of the polymeric tube, or characterized by a degradation rate profile characterized by varying degradation rates through predefined portions of a wall of the oriented polymeric tube, including a degradation rate profile characterized by an increasing degradation rate gradient through a wall from the inner diameter to the outer diameter of the polymeric tube and a degradation rate profile characterized by a decreasing degradation rate gradient through a wall from the inner diameter to the outer diameter of the oriented polymeric tube. In some embodiments, oriented polymeric tubes are provided herein which are characterized by a degradation rate profile that is substantially consistent through a length of the oriented polymeric tube, characterized by a degradation rate profile that is substantially consistent along a length of the oriented polymeric tube, or characterized by a degradation rate profile characterized by varying degradation rates along the length of the oriented polymeric tube, including a degradation rate profile characterized by a degradation rate gradient along the length of the oriented polymeric tube.

Advantageously, oriented polymeric tubes provided according to the present disclosure can exhibit sufficient strength, e.g., for in vivo use. Such tubes can be characterized as having sufficient compression strength/resistance to radial compression to function in the desired context. For example, in some embodiments, oriented polymeric tubes provided according to the disclosed methods may find use, e.g., as stents or as components of stents. Stents are subjected to heavy loads, e.g., when inserted and left in blood vessels and should exert a radial force sufficient to ensure that the stent remains in the narrowed spot and prevent constricting of blood vessels. Oriented polymeric tubes prepared by the foregoing methods were tested (e.g., to evaluate cyclic compression), and relevant findings from this testing are described herein below. Certain oriented polymeric tubes prepared according to the planar orientation/annular positioning method exhibited higher energy absorption (normalized for wall thickness) than the comparative material (prepared via traditional extrusion/expansion methods as described herein). All tested oriented polymeric tubes prepared according to the planar orientation/annular positioning methods showed improved hysteretic behavior as measured by the x-intercept at the start of each cycling period.

It was also found that various parameters of the disclosed methods (and properties of the disclosed materials) can lead to differences in physical properties of the resulting oriented polymer tubes, allowing for flexibility in processing. For example, the physical properties of oriented polymeric tubes can be modified based on the present disclosure, e.g., by selecting a polymer with a different molecular weight and/or composition (e.g., including copolymers), by modifying the manner of orientation of the film in the planar orientation/annular positioning method (e.g., uniaxial vs biaxial), wrapping polymeric films/profiles at a different angle around a forming mandrel (e.g., along an axis or on a bias angle), employing different polymer films/profiles wrapped together at the mandrel, wrapping such polymer films/profiles in different ways (e.g., staggered versus stacked), etc. In some embodiments, the disclosed method comprises arranging a plurality of units of stretched polymeric material (e.g., stretched films/profiles, etc.) in at least one of a stacked manner and a staggered manner, and wrapping the arranged plurality of units of stretched polymeric material on a bias angle, where the bias angle can vary (including 0°).

The end use of the tubes provided according to the present disclosure can vary. As referenced herein, the molecular orientation afforded by the disclosed methods advantageously can provide tubes of relatively high strength (e.g., radial/compression strength), making these tubes particularly useful where such high strengths are important. One such application is in the context of medical implants such as stents. The sizes of stents provided according to certain embodiments of the disclosed method can vary, and may be suitably designed for one or more specific applications. For example, in some embodiments, the length, L of the stent may be from about 20 mm to about 200 mm. For example, for some applications, the stent may have a length, L, of from about 40 mm to 100 mm or any value between, for example, at least about 50 mm, 60 mm, 70 mm, 80 mm, or 90 mm. In some applications, the stent may have a length, L, of from about 25 mm to 150 mm or any value between, for example at least about 50 mm, 75 mm, 100 mm or 125 mm. The stent may also be longer or shorter than these exemplary values in other stent applications. Likewise, in some embodiments, the strut thickness of the stent may be from about 0.7 mm to about 0.4 mm. For example, for some applications, the stent may have a strut thickness of from about 0.08 mm to 0.15 mm or any value between, for example, at least about 0.09 mm, 0.1 mm, 0.12 mm, 0.13 mm, or 0.14 mm. In some applications, the stent may have a strut thickness of from about 0.15 mm to 0.4 mm or any value between, for example at least about 0.2 mm, 0.25 mm, 0.3 mm or 0.35 mm. The stent may also have a strut thickness greater than or less than these exemplary values in other stent applications. Likewise the stent may be formed with a variety of diameters. In some embodiments the midbody diameter of the stent (the diameter of the stent at a point equidistant from each end) may be from about 1.5 mm to about 40 mm, such as a midbody inside diameter of about 2.5 mm to 16 mm or any distance within this range such as between about 3 mm to 14 mm or between about 5 mm to about 10 mm.

Stents are generally cylindrically shaped devices often used in the treatment of arterial disease. Arterial disease involves the deposition of lipids within an artery and subsequent plaque formation along the arterial wall. These plaque lesions may be soft or become hard and calcified and over time reduce the luminal space within the vessel, a process known as stenosis. To treat stenosis, stents are commonly deployed at the treatment site serving to maintain patency of the lumen of the diseased segment of the vessel. Stents must have adequate radial strength to provide the vessel with adequate radial support to maintain vessel patency.

Stents are commonly manufactured by laser cutting a tube to into a radially expandable geometry comprising interconnected structural elements or struts. During conventional deployment as with an angioplasty balloon catheter, the stent struts undergo high localized deformation, requiring the material from which the stents are manufactured to be highly deformable while maintaining high strength and rigidity (e.g. the material must exhibit high toughness). In many clinical treatment applications, the stent is required only temporarily, for example, to maintain patency during a critical healing phase or to deliver an active agent or a drug to a target site.

As such, tubes described herein may find particular use as stents, as they can, in various embodiments, exhibit high compressive/radial strength as well as biodegradability/bioabsorbability. The ability to tailor the composition and physical properties of the layers that comprise each tube, as disclosed herein, allows for the production of tubes exhibiting sufficient compressive/radial strength, as well as biodegradability, which can, e.g., be completely absorbed after their clinical utility has ended. The tubes disclosed herein can be processed/modified accordingly to serve a desired purpose in this regard, e.g., by cutting into an appropriate size/geometry.

In other embodiments, the tubes provided according to the present disclosure can be used in other contexts, e.g., including but not limited to, serving as heat shrink tubes to be placed around other tubes/tubular constructs, e.g., to aid in fusing components of such tubular constructs. In some embodiments, such heat shrink tubes prepared according to the disclosed methods exhibit enhanced thermodynamic properties, including, but not limited to, improved heat shrink capabilities.

Although the present disclosure focuses on embodiments comprising at least one crystallizable (e.g., crystallizable, biodegradable) polymer, it is noted that the principles described herein are not limited thereto. Although the techniques outlined herein are advantageously applied in the context of such crystallizable polymers to orient molecules therein for enhanced strength of the resulting tubular form, these principles can provide other benefits as well, which are not limited to crystallizable polymers (and may be applicable, e.g., to amorphous polymers, including, but not limited to, biodegradable amorphous polymers). As such, in some embodiments, the disclosure provides methods for subjecting a polymeric material comprising an amorphous biodegradable polymer to planar stretching and annular orientation or to multilayer annular expansion and annular positioning as generally disclosed herein. Typically, such amorphous polymer-containing products do not exhibit the high strength values referenced herein above with respect to crystallizable polymer-containing products (which are enhanced, e.g., by molecular orientation), and thus may find use, e.g., in the processing of other tubes (e.g., including, but not limited to, serving as a heat shrink material to fuse other multi-layer tubes as referenced above) and as a component of various devices, e.g., being reinforced by one or more additional components.

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

EXAMPLE 1

A plaque consisting of PL32, a polylactide resin purchased from Corbion Purac, was created via compression-molding to a thickness of 125 μm using a Carver Press. The PL32 plaque was then stretched uniaxially in a Brückner Lab Stretcher to give a final thickness of around 25 μm. A plaque consisting of PLC 7015, a copolymer resin of lactide and caprolactone obtained from Corbion Purac, was created via compression-molding to yield a thickness of around 40 μm using a Carver Press. The PLC7015 plaque was then stretched biaxially in a Brückner Lab Stretcher to a final thickness of around 15 μm.

Rectangles were cut out of each of the two films and placed one on top of the other and wrapped around a metal mandrel with OD=2.8 mm with the PL32 film in contact with the mandrel. The films were wrapped such that the stretch direction of the PL32 film was aligned in the circumferential direction. The wrapped mandrel was then covered tightly with a linear low density polyethylene (LLDPE) film, Cortuff® Shrink Film obtained from the Sealed Air Corporation, and taped into place. The assembly was subsequently placed into a hot air circulating oven set at 80° C. for 30 minutes. After the assembly was taken out of the oven, the shrink film was removed, and the now-fused composite tube was slid off of the mandrel. The final mean wall thickness of the composite tube was around 130 μm.

EXAMPLE 2

The procedure of Example 1 was repeated starting with a 125 μm plaque made from PL65 polylactide purchased from Corbion Purac stretched uniaxially to a final thickness of around 30 μm and a 40 μm plaque made from PLC 7015 stretched biaxially to a final thickness of around 15 μm. The pressure-formed tube had a wall thickness of around 140 μm.

EXAMPLE 3

The procedure of Example 1 was repeated using an oven temperature of 120° C.

EXAMPLE 4

The procedure of Example 2 was repeated using an oven temperature of 120° C.

EXAMPLE 5

The procedure of Example 1 was repeated using an oven temperature of 160° C.

EXAMPLE 6

The procedure of Example 2 was repeated using an oven temperature of 160° C.

EXAMPLE 7

The procedure of Example 1 was repeated using an oven temperature of 180° C.

EXAMPLE 8

The procedure of Example 2 was repeated using an oven temperature of 180° C.

Cyclic Compression Testing

The composite tubes from Examples 1 through 8 were tested in compression on an Instron machine with a 10 lb load cell. The tube was positioned such that its length axis was normal to the movement of the jaw. During the test, a disk clamped to the jaw was lowered onto the tube surface.

Compression of the tube occurred until the tube had been deformed to 50% of its initial diameter at 50% of its initial diameter per minute, whereupon the jaw moved back up to its starting position at the same rate. The force required to compress the sample was measured by the load cell and converted to a stress. The procedure was repeated five times per tube with no dwell between cycles. The values reported were the maximum stress, the energy absorbed by the tube over the five cycles normalized for wall thickness, and the recovery of the tube as a percent of the compression extent. This last quantity is an indication of the hysteresis between compression cycles for the tube.

Figure 6A:
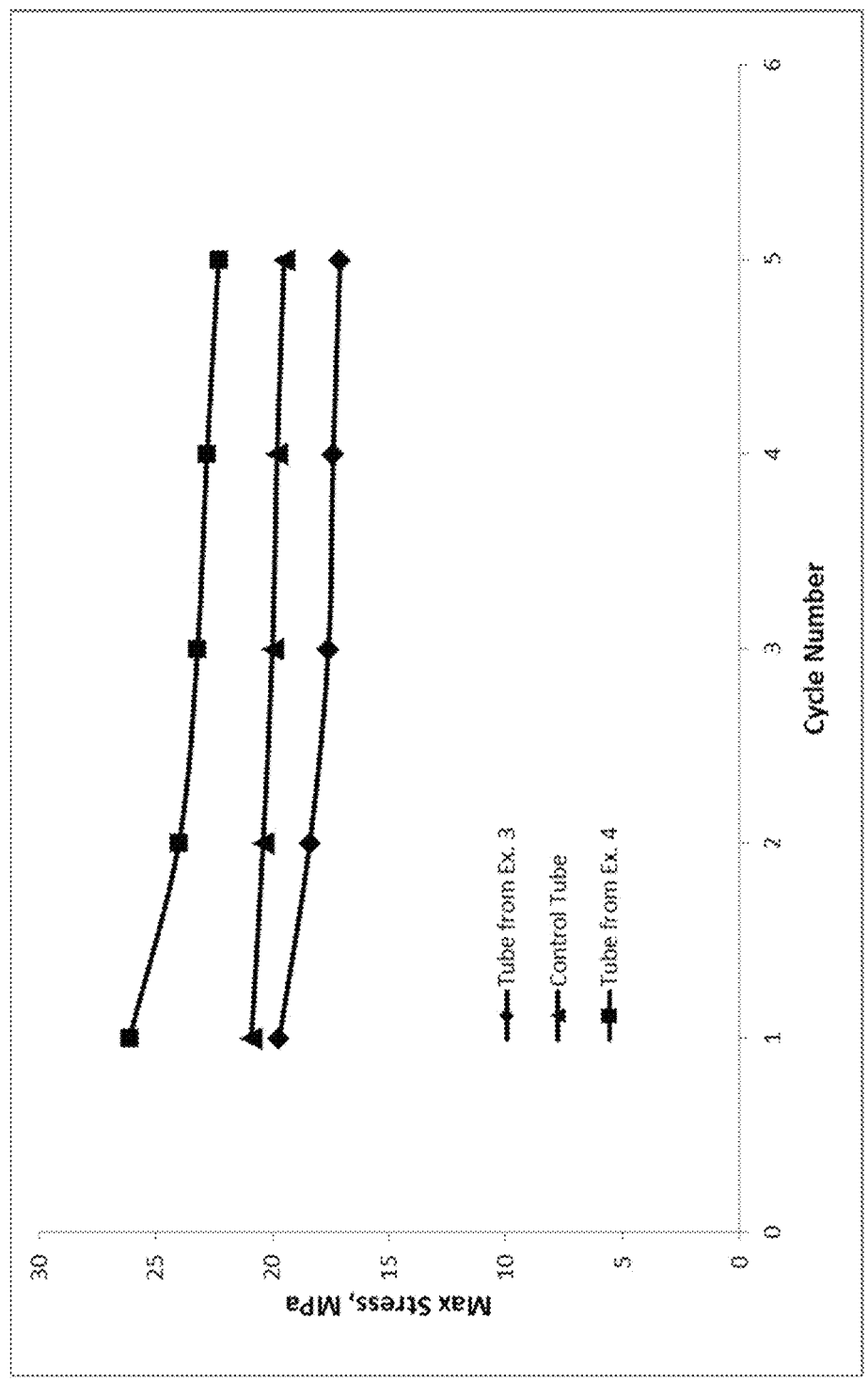
FIGS. 6A, 6B, 6C. show Max Stress, Normalized Energy and X-Intercept from cyclic compression tests for the Tubes from Example 3 and Example 4 compared to a control tube.
Figure 6B:
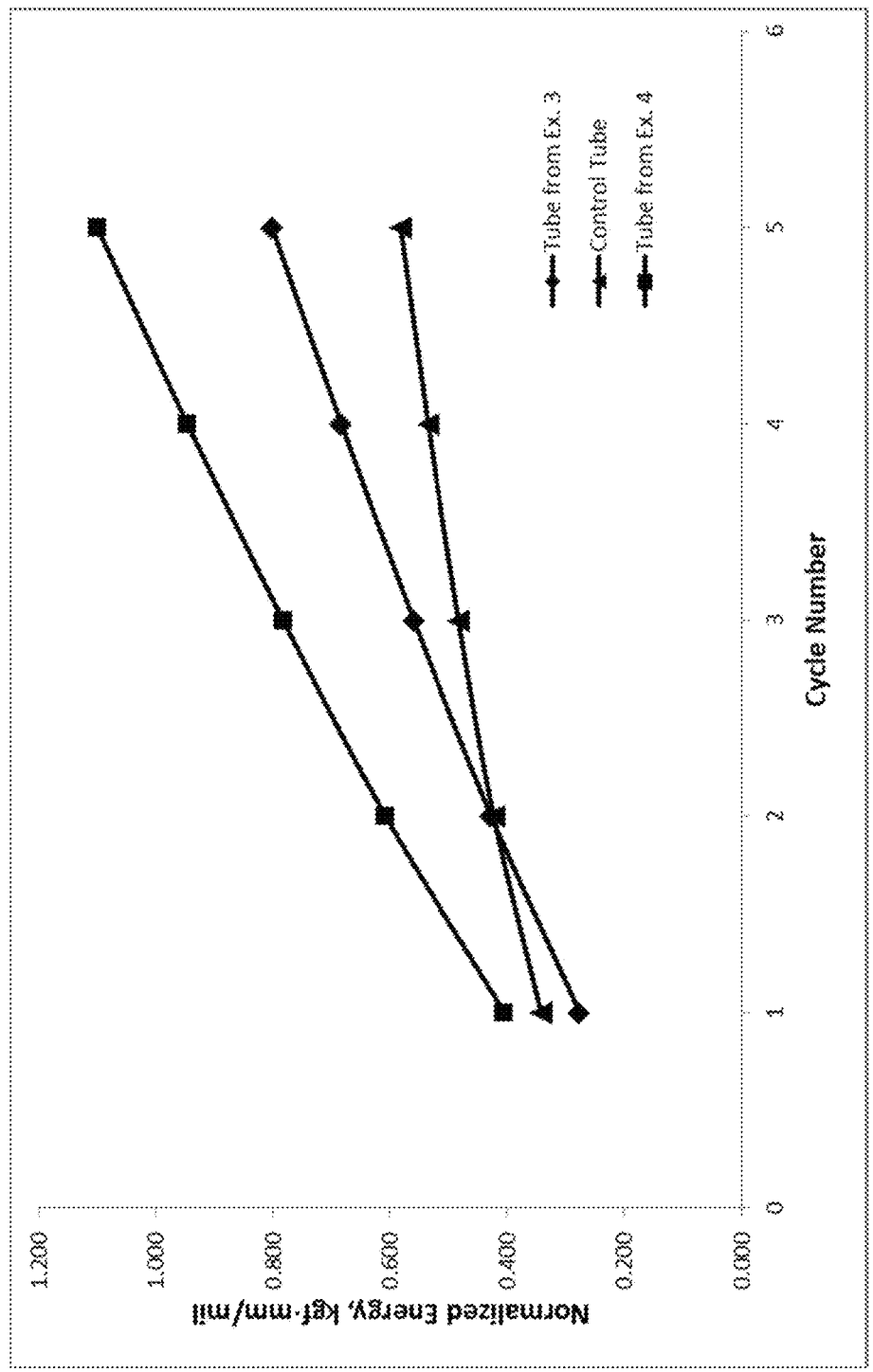
Figure 6C:
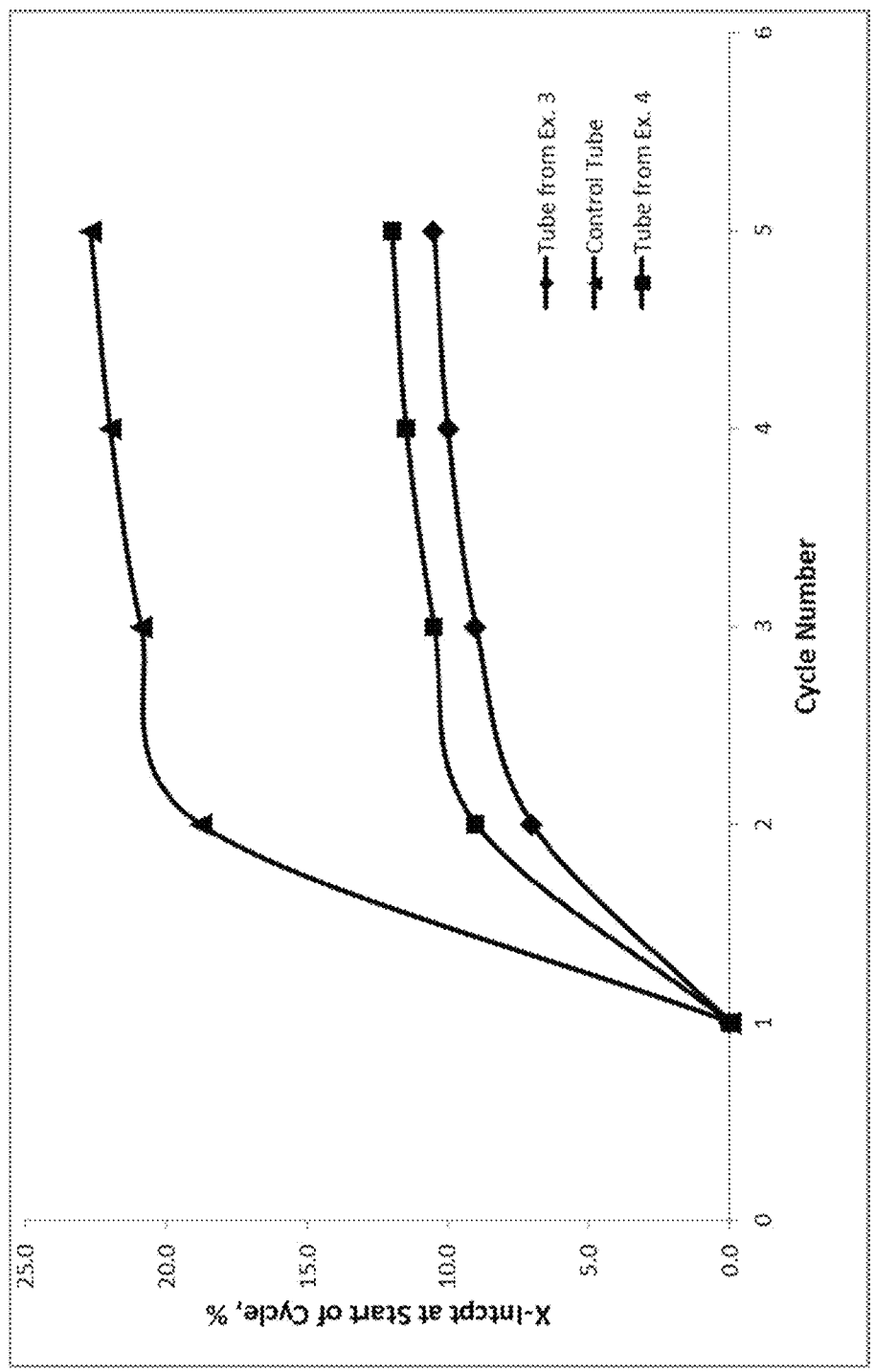

FIGS. 6A, 6B, 6C. show Max Stress, Normalized Energy and X-Intercept from cyclic compression tests for the tubes from Example 3 and Example 4 compared to a control tube. The control tube was manufactured by extruding and expanding an input tube consisting of PL38 PLLA from Corbion Purac to a final dimension of 2.8 mm ID with a wall thickness of 100 μm. The tube was then annealed at 120° C. for 30 minutes to match the pressure-forming time of the composite tubes from Examples 3 and 4. From FIGS. 6A, 6B, 6C, the tube from Ex. 4 shows clear superiority to the control tube in Max Stress, Normalized Energy and hysteresis between cycles for all compression cycles. The tube from Ex. 3 shows lower Max. Stress values, but improvements in Normalized Energy and hysteresis between cycles.

Figure 7A:
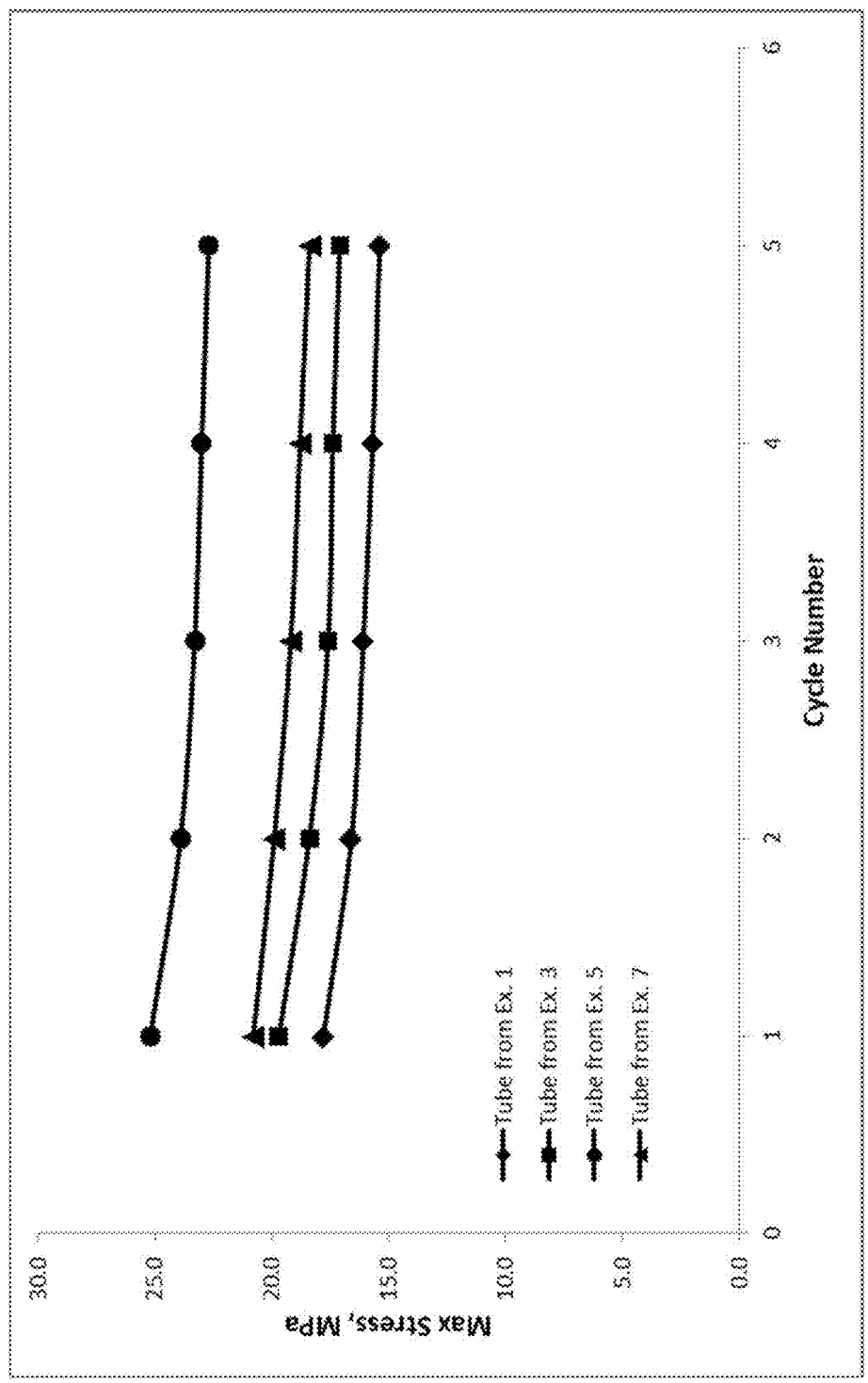
FIGS. 7A, 7B, 7C. show Max Stress, Normalized Energy and X-Intercept from the cyclic compression tests for the Tubes from Examples 1, 3, 5 and 7.
Figure 7B:
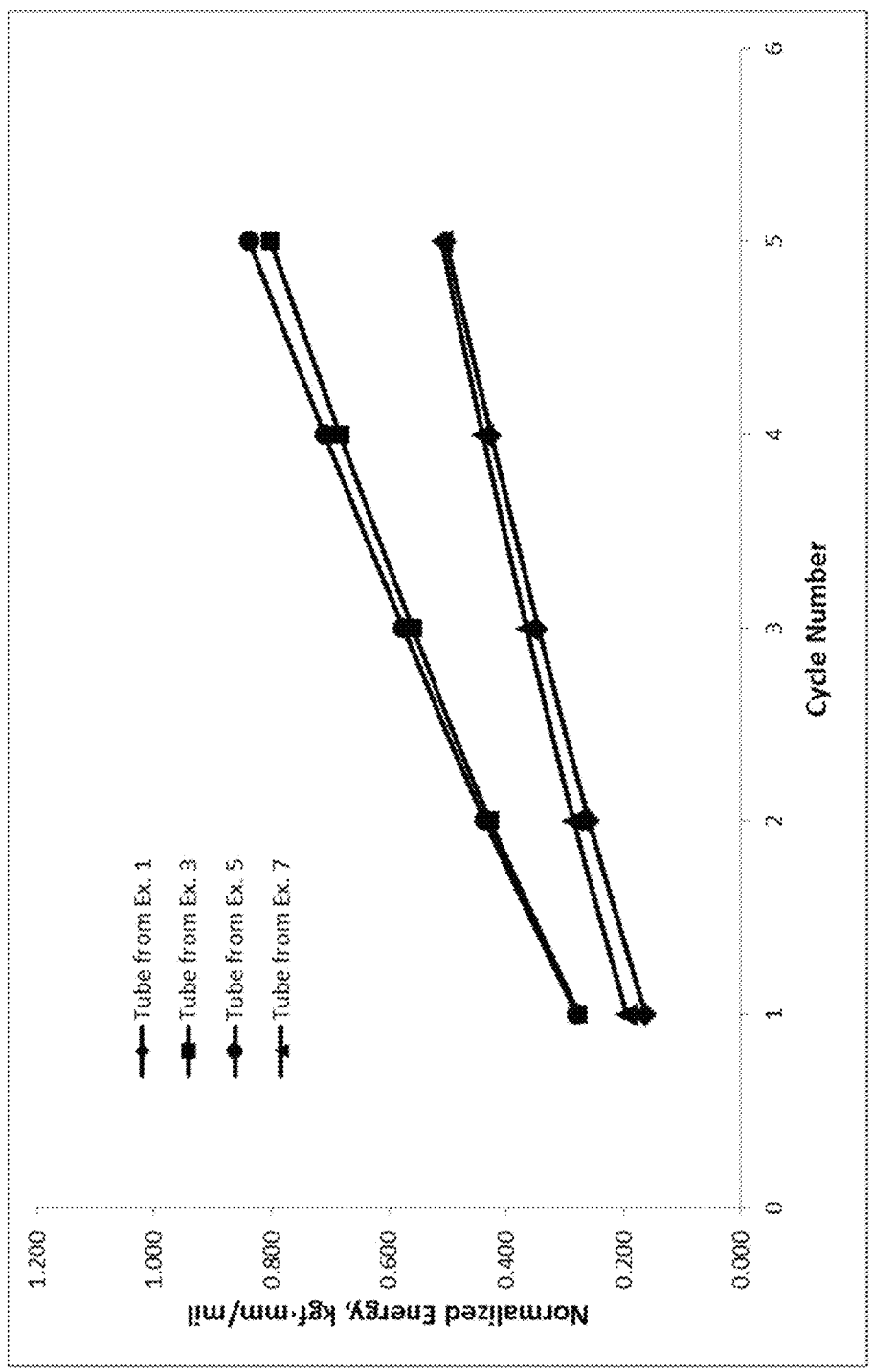
Figure 7C:
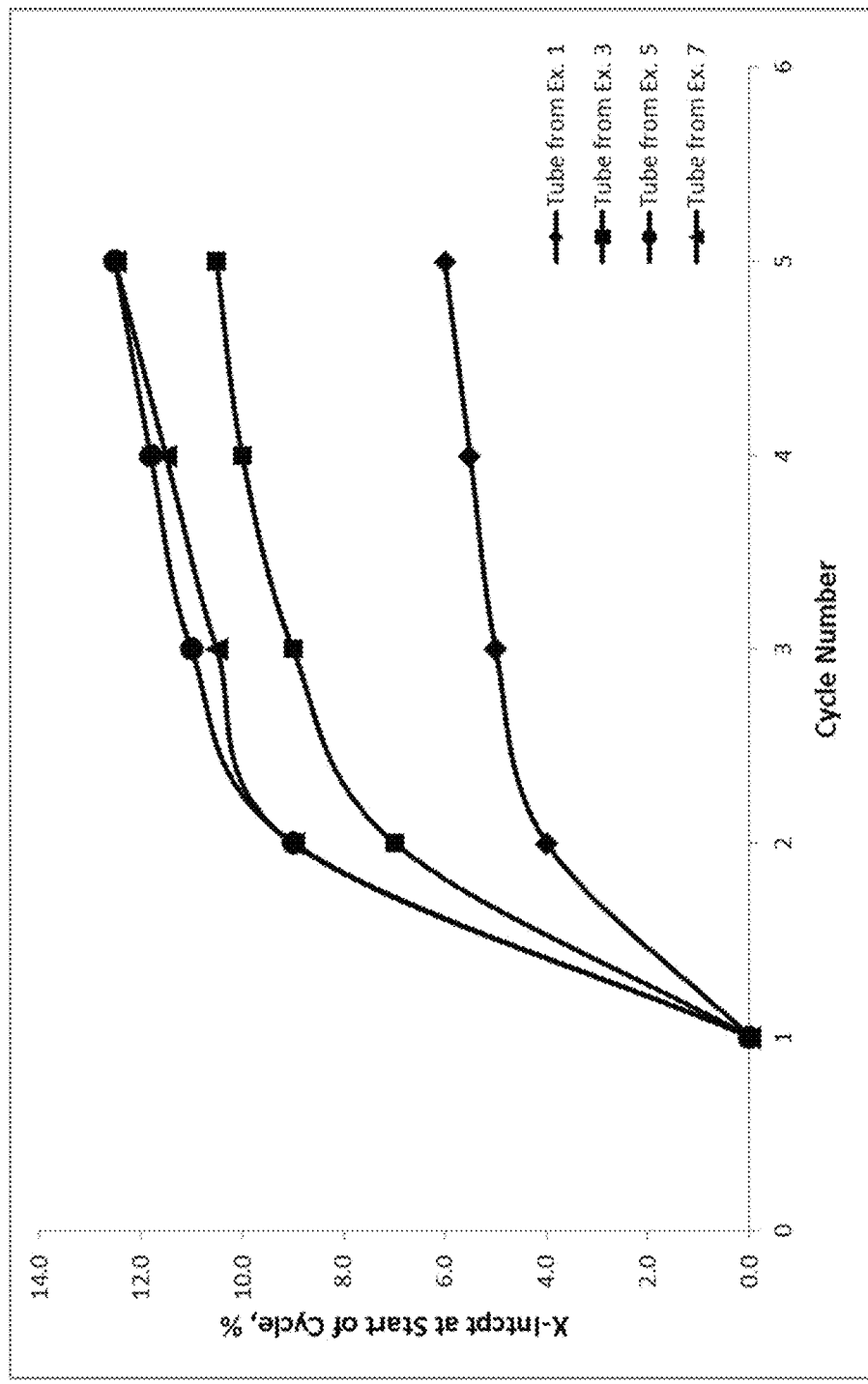

FIGS. 7A, 7B, 7C. show Max Stress, Normalized Energy and X-Intercept from the cyclic compression tests for the Tubes from Examples 1, 3, 5 and 7. The effects of forming temperature on these properties are readily apparent. For the PL32/PLC7015 composite structure disclosed in the examples, the optimum forming temperature to maximize Max Stress and Energy is 160° C.

Figure 8A:
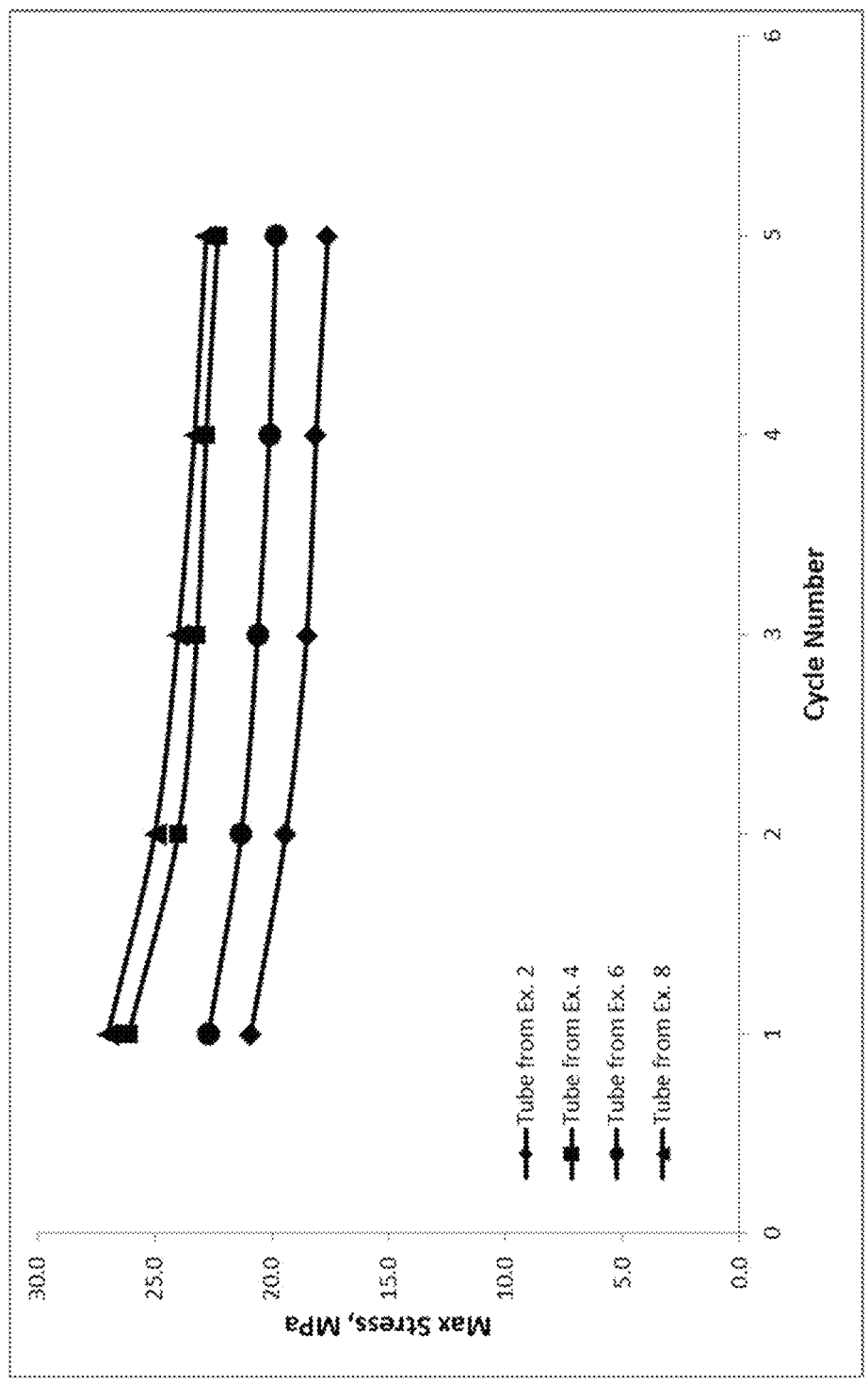
FIGS. 8A, 8B, 8C. show Max Stress, Normalized Energy and X-Intercept from the cyclic compression tests for the Tubes from Examples 2, 4, 6 and 8.
Figure 8B:
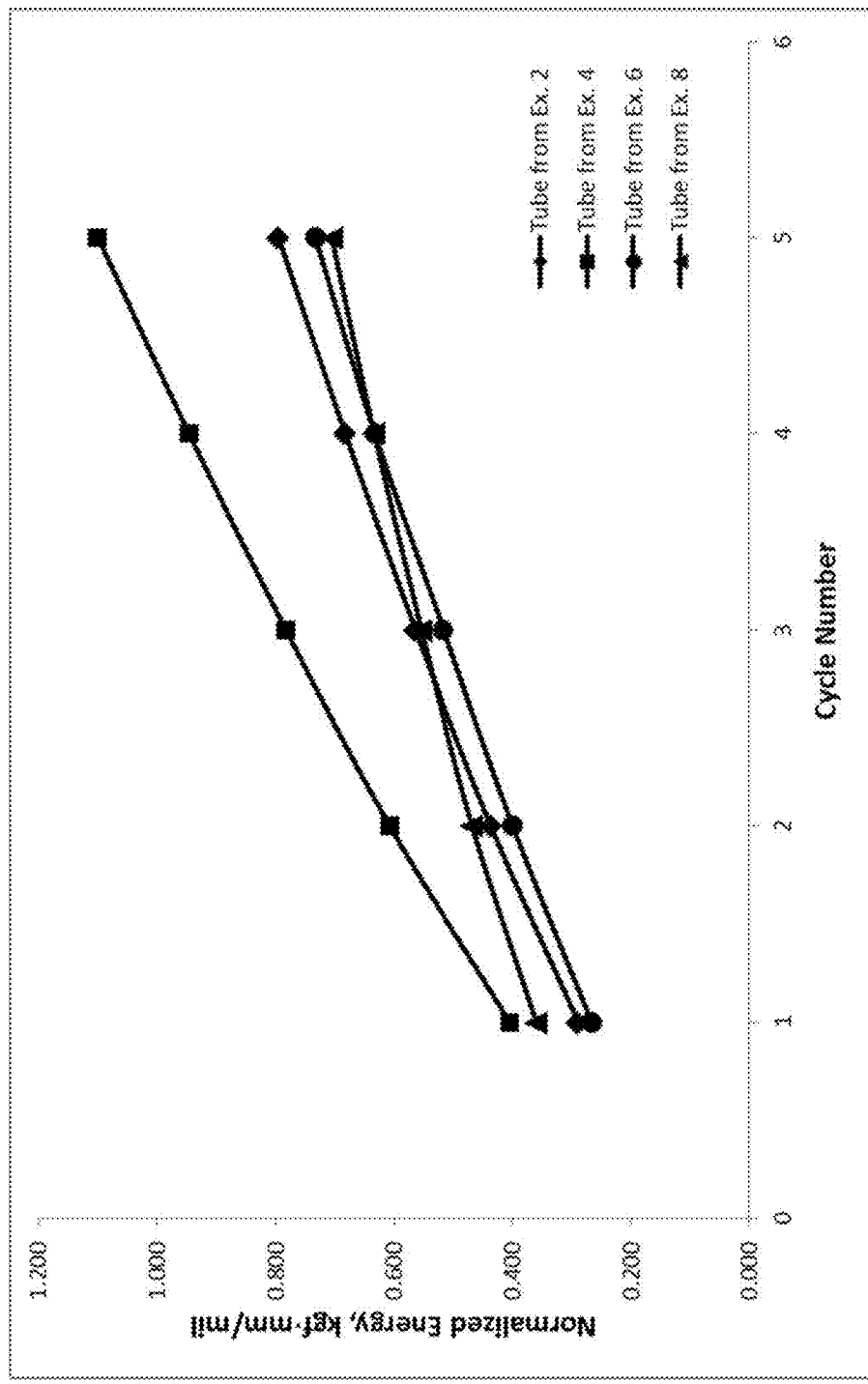
Figure 8C:
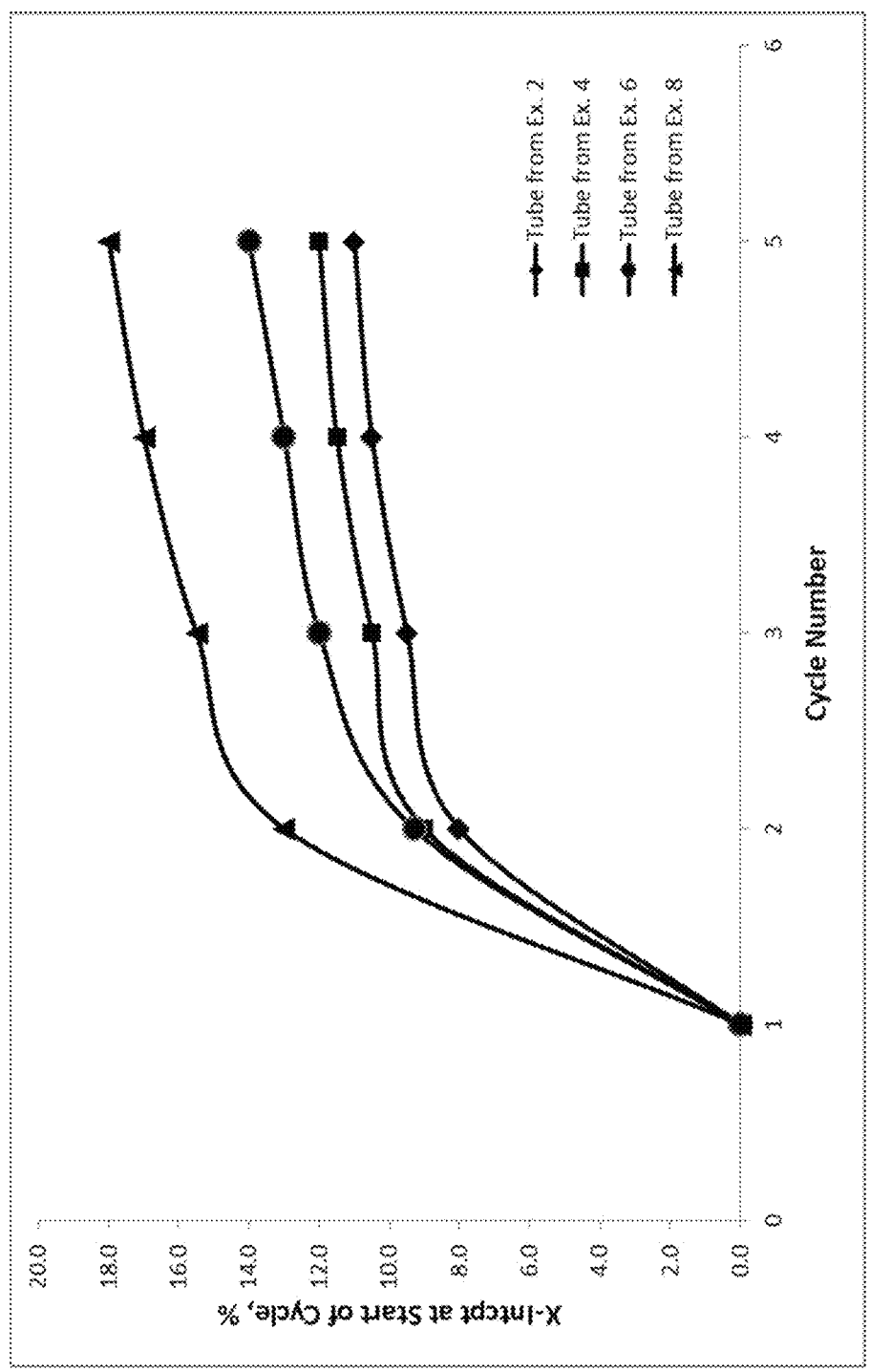

FIGS. 8A, 8B, 8C. show Max Stress, Normalized Energy and X-Intercept from the cyclic compression tests for the Tubes from Examples 2, 4, 6 and 8. For the PL65/PLC7015 composite structure disclosed in the examples, the optimum forming temperature to maximize Max Stress and Energy is 120° C.

EXAMPLE 9

The procedure of Example 3 was repeated starting with a 125 μm plaque made from PL32 that was stretched biaxially to a final thickness of about 10 μm and a 40 μm plaque made from PLC 7015 that was stretched biaxially to a final thickness of around 15 μm. The finished composite tube had a mean wall thickness of around 120 μm.

EXAMPLE 10

The procedure of Example 3 was repeated starting with a 125 μm plaque made from PL32 that was stretched biaxially to a final thickness of about 10 μm and a 125 μm plaque made from PLC8516, polylactide-co-caprolactone copolymer purchased from Corbion Purac, that was stretched biaxially to a final thickness of about 7 μm. The finished composite tube had a mean wall thickness of around 50 μm.

EXAMPLE 11

The procedure of Example 4 was repeated using a 125 μm plaque made from PLC8516 that was stretched uniaxially to a final thickness of about 25 μm and a 125 μm plaque made from PLC8516, a polylactide-co-caprolactone copolymer purchased from Corbion Purac, which was stretched biaxially to a final thickness of about 7 μm. The finished composite tube had a mean wall thickness of around 95 μm.

EXAMPLE 12

The procedure of Example 3 was repeated using a 125 μm plaque made from PLC8516 that was stretched biaxially to a final thickness of about 7 μm and a 45 μm plaque made from PC12, polycaprolactone purchased from Corbion Purac, that was stretched biaxially to a final thickness of about 25 μm. The finished composite tube had a mean wall thickness of around 100 μm.

EXAMPLE 13

A 125 μm plaque made from PLC8516 was stretched biaxially to a final thickness of about 7 μm. A rectangle was cut out of the film and wrapped around a metal mandrel with OD=2.8 mm. The wrapped mandrel was then covered tightly with a LLDPE shrink film and taped into place. The assembly was subsequently placed into a hot air circulating oven set at 120° C. for 30 minutes. After the assembly was taken out of the oven, the shrink film was removed, and the now-fused composite tube was slid off of the mandrel. The final mean wall thickness of the composite tube was around 90 μm.

EXAMPLE 14

A plaque consisting of PL32 was molded to a thickness of 125 μm and stretched biaxially in a Brückner Lab Stretcher to give a final thickness of around 15 μm. A plaque consisting of PLC 7015 was molded to give a thickness of 40 μm, and then it was stretched biaxially to yield a final thickness of around 15 μm. A 125 μm plaque made from PLC8516 was stretched biaxially to a final thickness of about 7 μm. Rectangles were cut out of each of the films, stacked in the order PL32/PLC7015/PLC8516 and wrapped around a metal mandrel with OD=2.8 mm. The PL32 film was in contact with the mandrel. The wrapped mandrel was then covered tightly with a LLDPE film and taped into place. The assembly was subsequently placed into a hot air circulating oven set at 120° C. for 30 minutes. After the assembly was taken out of the oven, the shrink film was removed, and the now-fused composite tube was slid off of the mandrel. The final mean wall thickness of the composite tube was around 80 μm.

EXAMPLE 15

A 30 μm wall, 2.8 mm ID extruded and expanded tube made from PL32 resin (PLA) was slid over a mandrel, and the biaxially stretched PL32 film and PLC7015 film from Example 9 were wrapped around the PLA tube with the PLC7015 film contacting the outer circumference of the PLA tube. The wrapped mandrel was then covered tightly with a LLDPE film and taped into place. The assembly was subsequently placed into a hot air circulating oven set at 120° C. for 30 minutes. After the assembly was taken out of the oven, the shrink film was removed, and the now-fused composite tube was slid off of the mandrel. The final mean wall thickness of the composite tube was around 130 μm.

What is claimed is:
1. A method for producing a multilayered tube, comprising:
stretching at least one polymeric material, which comprises at least one crystallizable biodegradable poly- meric material and has a first dimension, wherein the stretching is performed in a manner that increases the first dimension and that results in a controlled level of orientation;
forming a multilayered tube using the at least one polymeric material and at least one adhesive material layer or forming a multilayered tube using the at least one stretched polymeric material and at least one adhesive material layer, wherein the multilayer tube has an orientation profile that is substantially consistent throughout a wall of the multilayered tube.

2. The method of claim 1, wherein the stretching the at least one polymeric material comprises planar stretching.

3. The method of claim 1, wherein one or more of the at least one polymeric material is one or more of a polymer film, a polymer monofilament, a polymer tape, and a polymer rod.

4. The method of claim 1, wherein:
the at least one polymeric material has a second dimension, and
the stretching the at least one polymeric material comprises stretching the at least one polymeric material to increase the second dimension,
such that the at least one stretched polymeric material comprises a biaxially stretched polymeric material.

5. The method of claim 1, wherein the at least one adhesive polymeric material layer is in contact with the at least one stretched polymeric material before, during, or after the stretching of the at least one polymeric material.

6. The method of claim 1, further comprising:
obtaining the at least one polymeric material based at least in part on combining the at least one adhesive material layer with the at least one crystallizable biodegradable polymeric material.

7. The method of claim 6, wherein the at least one polymeric material is a composite polymeric material comprising the at least one crystallizable biodegradable polymeric material and the at least one adhesive material layer in layered form.

8. The method of claim 6, wherein the at least one adhesive material layer and the at least one crystallizable biodegradable polymeric material are combined before, during, or after the at least one polymeric material is stretched.

9. The method of claim 1, wherein the forming the tube comprises wrapping the at least one stretched polymeric material and the at least one adhesive material layer around a support.

10. The method of claim 9, wherein the support has one or more of a cylindrical shape, a round shape, a rectangular shape, a triangular shape, an elliptical shape, a polygonal shape, and a tubular form.

11. The method of claim 9, wherein the wrapping comprises wrapping the at least one stretched polymeric material and the at least one adhesive material layer around the support multiple times such that the multilayered tube comprises multiple layers of the at least one stretched polymeric material and multiple layers of the at least one adhesive material layer.

12. The method of claim 9, wherein:
the at least one stretched polymeric material comprises a plurality of units of stretched polymeric material,
the plurality of units of stretched polymeric material comprises different polymeric materials or a same polymeric material; and
the forming the multilayered tube comprises arranging the plurality of units of stretched polymeric material in at least one of a stacked manner and a staggered manner, and wrapping the arranged plurality of units of stretched polymeric material on a bias angle.

13. The method of claim 9, wherein the support is a mandrel, and the method further comprises removing the multilayered tube from the mandrel.

14. The method of claim 9, wherein the support comprises a device.

15. The method of claim 14, further comprising forming a resulting composite based at least in part on the multilayered tube and the support, and the resulting composite is a medical device.

16. The method of claim 1, further comprising forming a medical device based at least in part on the multilayered tube.

17. The method of claim 16, wherein the forming the medical device comprises:
cutting the multilayered tube into a stent.

18. The method of claim 17, further comprising applying one or more of a therapeutic, a covering, and a coating to the stent.

19. The method of claim 1, wherein the forming the tube comprises subjecting the at least one stretched polymeric material to at least one of heat and pressure.

20. The method of claim 1, wherein the forming the tube comprises:
forming a layered structure, the forming the layered structure comprising:
applying a shrink tube or shrink film around at least part of the at least one stretched polymeric material to give a layered structure, and
subjecting the layered structure to at least one of heat and pressure.

21. The method of claim 1, wherein the forming the tube comprises:
inserting at least part of the at least one stretched polymeric material in a mold;
positioning the at least one stretched polymeric material over an expandable support; and
subjecting the at least one stretched polymeric material to at least one of heat and pressure.

22. The method of claim 1, wherein one or more of the at least one crystallizable biodegradable polymeric material is selected from the group consisting of poly(L-lactide) (PLLA), poly(D-lactide) (PDLA), poly(ε-caprolactone) (PCL), polyglycolic acid (PGA), poly(para-dioxanone) (PDO), poly(hydroxybutyrate), poly(hydroxyvalerate), poly(tetramethyl carbonate), poly(ethylene oxide) (PEO), poly(ethylene glycol) (PEG), poly(propylene glycol) (PPG), and copolymers and derivatives and combinations thereof.

23. The method of claim 1, wherein the adhesive polymeric material is selected from the group consisting of poly(ε-caprolactone), poly(trimethylene carbonate), poly(D,L-lactide), poly(L-lactide)-co-ε-caprolactone), poly(L-lactide-co-trimethylene carbonate), poly(ε-caprolactone-co-trimethylene carbonate), poly(ethylene glycol), poly(L-lactide-co-poly(ethylene glycol)), and copolymers and derivatives and combinations thereof.

24. The method of claim 5, wherein the forming the tube comprises using the at least one stretched polymeric material and at least one adhesive polymeric material, and the at least one crystallizable biodegradable polymeric material and the at least one adhesive polymeric material comprise a same polymeric material.

25. The method of claim 1, wherein the at least one stretched polymeric material is stretched at least ten percent of a maximum stretch ratio respectively corresponding to the at least one polymeric material.

26. The method of claim 1, wherein the stretching the at least one polymeric material comprises controlling, during the stretching, one or more of a mechanical property, a thermodynamic property, a chemical property, an electrical property, and a degradation rate, of the at least one polymeric material.

27. The method of claim 1, wherein the at least one polymeric material is stretched between three hundred percent and one thousand percent of an original dimension of the at least one polymeric material.

28. The method of claim 1, further comprising stretching the multilayered tube.

29. A method, comprising:
obtaining at least one stretched polymeric material exhibiting at least partial molecular orientation, wherein:
the at least one stretched polymeric material comprises at least one crystallizable biodegradable polymeric material, wherein the at least one stretched polymeric material has a first dimension, and wherein the at least one stretched polymeric material was prepared by stretching at least one polymeric material in a manner that increased the first dimension and that resulted in a controlled level of orientation;
forming a multilayered tube using the at least one stretched polymeric material and at least one adhesive material layer, wherein the multilayer tube has an orientation profile that is substantially consistent throughout a wall of the multilayered tube.

30. The method of claim 29, further comprising stretching the multilayered tube.

* * * * *